(12) United States Patent
Rabinovich et al.

(10) Patent No.: US 10,000,548 B2
(45) Date of Patent: Jun. 19, 2018

(54) GAL-1 VARIANTS HAVING IMMUNO-MODULATING PROPERTIES AND METHODS OF USING THE SAME

(71) Applicants: CONSEJO NACIONAL DE INVESTIGACIONES CIENTÍFICAS Y TÉCNICAS, Buenos Aires (AR); FUNDACIÓN SALES, Buenos Aires (AR); INIS BIOTECH LLC, Milford, DE (US)

(72) Inventors: Gabriel Adrián Rabinovich, Buenos Aires (AR); Santiago Di Lella, Berlin (DE); Dario Ariel Estrin, Buenos Aires (AR); Julio Javier Carmelo, Buenos Aires (AR); Santiago Patricio Mendez Huergo, Caba CP (AR)

(73) Assignees: Consejo Nacional de Investigaciones Cientificas Y Técnicas, Buenos Aires (AR); Fundación Sales, Buenos Aires (AR); INIS Biotech LLC, Milford, DE (US)

( * ) Notice: Subject to any disclaimer, the term of this patent is extended or adjusted under 35 U.S.C. 154(b) by 0 days. days.

(21) Appl. No.: 15/567,390

(22) PCT Filed: Apr. 21, 2016

(86) PCT No.: PCT/US2016/028604
§ 371 (c)(1),
(2) Date: Oct. 18, 2017

(87) PCT Pub. No.: WO2016/172319
PCT Pub. Date: Oct. 27, 2016

(65) Prior Publication Data
US 2018/0105571 A1 Apr. 19, 2018

Related U.S. Application Data

(60) Provisional application No. 62/150,570, filed on Apr. 21, 2015, provisional application No. 62/151,121, filed on Apr. 22, 2015.

(51) Int. Cl.
*A61K 38/00* (2006.01)
*C07K 14/705* (2006.01)

(52) U.S. Cl.
CPC .......... *C07K 14/7056* (2013.01); *A61P 11/06* (2018.01); *A61P 19/02* (2018.01); *A61P 25/16* (2018.01); *A61P 25/28* (2018.01); *A61P 29/00* (2018.01); *A61P 37/08* (2018.01); *A61K 38/00* (2013.01)

(58) Field of Classification Search
None
See application file for complete search history.

(56) References Cited

U.S. PATENT DOCUMENTS

| 6,890,531 | B1 | 5/2005 | Horie et al. |
|---|---|---|---|
| 2003/0109464 | A1* | 6/2003 | Huflejt et al. |
| 2007/0098701 | A1 | 5/2007 | Okano et al. |
| 2010/0120146 | A1 | 5/2010 | Okano et al. |

OTHER PUBLICATIONS

PCT International Search Report and Written Opinion for PCT Application No. PCT/US2016/028604 dated Aug. 25, 2016 (8 pages).
Meynier et al., "NMR and MD Investigations of Human Galectin-1/Oligosaccharide Complexes," Biophysical Journal, 2009, 97:3168-3177.

* cited by examiner

*Primary Examiner* — Jeanette M Lieb
(74) *Attorney, Agent, or Firm* — Eversheds Sutherland (US) LLP

(57) ABSTRACT

Galectin-1 polypeptide variants that include a mutation of the histidine residue corresponding to position 52 of the full-length amino acid sequence of native human Gal-1 as shown in SEQ ID NO: 1, the mutation being a substitution of the histidine to tyrosine or asparagine, providing resistance to acidosis otherwise resulting in deactivation of the native human Gal-1. The Galectin-1 polypeptide variants may include one or more additional mutation(s) of the cysteine residue corresponding to a position selected from 2, 16, 88, or combinations thereof of the full-length amino acid sequence of native human Gal-1 as shown in SEQ ID NO: 1, the additional mutation being a substitution of the cysteine to serine, and providing resistance to oxidation.

20 Claims, 11 Drawing Sheets

SEQUENCE LISTING

```
<160> NUMBER OF SEQ ID NOS: 24

<210> SEQ ID NO 1
<211> LENGTH: 134
<212> TYPE: PRT
<213> ORGANISM: Homo sapiens

<400> SEQUENCE: 1

Ala Cys Gly Leu Val Ala Ser Asn Leu Asn Leu Lys Pro Gly Glu Cys
1               5                   10                  15

Leu Arg Val Arg Gly Glu Val Ala Pro Asp Ala Lys Ser Phe Val Leu
            20                  25                  30

Asn Leu Gly Lys Asp Ser Asn Asn Leu Cys Leu His Phe Asn Pro Arg
        35                  40                  45

Phe Asn Ala His Gly Asp Ala Asn Thr Ile Val Cys Asn Ser Lys Asp
    50                  55                  60

Gly Gly Ala Trp Gly Thr Glu Gln Arg Glu Ala Val Phe Pro Phe Gln
65                  70                  75                  80

Pro Gly Ser Val Ala Glu Val Cys Ile Thr Phe Asp Gln Ala Asn Leu
                85                  90                  95

Thr Val Lys Leu Pro Asp Gly Tyr Glu Phe Lys Phe Pro Asn Arg Leu
            100                 105                 110

Asn Leu Glu Ala Ile Asn Tyr Met Ala Ala Asp Gly Asp Phe Lys Ile
        115                 120                 125

Lys Cys Val Ala Phe Asp
    130
```

<210> SEQ ID NO 2
<211> LENGTH: 408
<212> TYPE: DNA
<213> ORGANISM: Homo sapiens

<400> SEQUENCE: 2

```
atggcttgtg gtctggtcgc cagcaacctg aatctcaaac ctggagagtg ccttcgagtg      60
cgaggcgagg tggctcctga cgctaagagc ttcgtgctga acctgggcaa agacagcaac     120
aacctgtgcc tgcacttcaa ccctcgcttc aacgcccacg gcgacgccaa caccatcgtg     180
tgcaacagca aggacggcgg ggcctggggg accgagcagc gggaggctgt ctttcccttc     240
cagcctggaa gtgttgcaga ggtgtgcatc accttcgacc aggccaacct gaccgtcaag     300
ctgccagatg gatacgaatt caagttcccc aaccgcctca acctggaggc catcaactac     360
atggcagctg acggtgactt caagatcaaa tgtgtggcct tgactga                   408
```

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

```
caacgccaac ggcgacgcca ac                                               22
```

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

```
gttggcgtcg ccgttggcgt tg                                               22
```

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

```
caacgcccag ggcgacgcca ac                                               22
```

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
gttggcgtcg ccctgggcgt tg                                               22
```

<210> SEQ ID NO 7
<211> LENGTH: 22
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 7
caacgcctat ggcgacgcca ac                                            22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gttggcgtcg ccataggcgt tg                                            22

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgtgcctgaa cttcaaccct cg                                            22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cgagggttga agttcaggca ca                                            22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgtgcctgta cttcaaccct cg                                            22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cgagggttga agtacaggca ca                                            22

<210> SEQ ID NO 13
<211> LENGTH: 18
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 13
atatggcttc tggtctgg                                                    18

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gtatatctcc ttcttaaagt taaac                                            25

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctggagagtc ccttcgagtg                                                  20

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gtttgagatt caggttgctg g                                                21

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
caaccttgtc cctgcacttc                                                  20

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ttgctgtctt tgcccaggtt c                                                21

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
                        primer

<400> SEQUENCE: 19
ccatcgtgtc caacagcaag                                              20

<210> SEQ ID NO 20
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tgttggcgtc gccgtg                                                  16

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cagaggtgtc catcaccttc                                              20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
caacacttcc aggctggaag                                              20

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
caagatcaaa tctgtggcct ttg                                          23

<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aagtcaccgt cagctgc                                                 17
```

GAL-1 VARIANTS HAVING IMMUNO-MODULATING PROPERTIES AND METHODS OF USING THE SAME

CROSS REFERENCE TO RELATED APPLICATIONS

This application claims the priority benefit of PCT/US2016/028604 filed on Apr. 21, 2016 which claims priority to U.S. Provisional Patent Application Nos. 62/150,570 filed on Apr. 21, 2015 and 62/151,121 filed Apr. 22, 2015. The contents of which are hereby incorporated by reference herein in their entirety.

INCORPORATION BY REFERENCE

Any references (patent application publications, issued patents, or journal publications) cited in the present disclosure are also incorporated by reference herein in their entireties. Also incorporated by reference are the Figures and any polynucleotide and polypeptide sequences that reference an accession number correlating to an entry in a public database, such as those maintained by The Institute for Genomic Research (TIGR) and/or the National Center for Biotechnology Information (NCBI).

SEQUENCE LISTING IDENTIFICATION

The Sequence Listing, which is a part of the present disclosure, includes a computer readable file (in .txt format) that was generated using the U.S. Patent and Trademark Office's PatentIn software and includes nucleotide and/or amino acid sequences of the invention. Said Sequence Listing, created on Apr. 20, 2016, is named 33858-0018 SL.txt and is 7,141 bytes in size. The subject matter of the Sequence Listing is incorporated by reference herein in its entirety.

FIELD OF INVENTION

The disclosure generally relates to novel Gal-1 variants, and using such variants in methods for modulating an immune response and treatment methods for conditions that would benefit from down-regulation of the immune response.

BACKGROUND

The immune system has evolved as a complex network of mechanisms to discriminate between 'self and non-self,' and homeostasis is reached by a tight control that leads to recognition and elimination of foreign antigens and/or development of tolerance. T-lymphocytes are one of the main characters of cellular immunity, as maintaining the balance between pro-inflammatory (Th1/Th17 cells) and anti-inflammatory (Th2/Treg) populations is essential for resolution of inflammation, keeping autoimmune and chronic inflammatory diseases at bay.

Amongst the different regulatory circuits that shape this equilibrium (immune homeostasis) are cell surface glycosylation and lectin-glycan signaling. Lectins are proteins with affinity for carbohydrates that induce particular cascade responses, and thus modulate the immune response. This regulation appears to be context dependent, namely: on the glycan side, different outcomes are achieved by programmed remodeling of the cell-surface glycome through the sequential actions of glycosidases and glycosyltransferases; and on the lectin side, microenvironmental conditions can alter lectin affinity and binding capability.

Galectins are members of a family of multifunctional lectins that are defined by their specificity for β-galactoside-containing glycans and a carbohydrate recognition domain (CRD). Cooper, D. N. W., "GALECTINOMICS: FINDING THEMES IN COMPLEXITY," *Biochimica et Byiophysica Acta*, General Subjects, 1572:209-231 (2002). In humans, CRDs have been identified for approximately 16 different galectins, a central example being Galectin-1 (Gal-1), a lectin that specifically binds N-acetyllactosamine terminal moieties exposed on cell surfaces and cross-links to a preferred set of glycosylated receptors to transduce signals that directly lead to Th1 and Th17 apoptosis and termination of the inflammatory response. Human Gal-1 is a small lectin composed of 135 amino acids, which folds into a three-dimensional structure in the form of a β-sandwich of two slightly bent sheets with variable long connecting loops. A notable feature of Gal-1 is the high proportion of cysteine residues (Pe'er et al., "PROTEOMIC SIGNATURES: AMINO ACID AND OLIGOPEPTIDE COMPOSITIONS DIFFERENTIATE AMONG PHYLA," *Proteins*, 54:20-40 (2004)), each Gal-1 monomer containing six cysteines: Cys2, Cys16, Cys60, Cys88, and Cys130.

Binding of Gal-1 depends on glycosyltransferase activity, including the activity of N-acetylglucosaminyltransferase 5 (GnT5), an enzyme responsible of generating β-1,6-N-glycan branch structures and a core 2 β-1,6 N-acetylglucosaminyltransferase (GCNT1) that elongates the core 2-O-glycans. Whereas Th1 cells and Th17 cells express the repertoire of cell surface glycans that are critical for Gal-1 binding and cell death, Th2 cells are protected from Gal-1 binding through α-2,6 sialylation of cell surface glycoproteins (Toscano et al., "DIFFERENTIAL GLYCOSYLATION OF $T_H1$, $T_H2$ AND $T_H$-17 EFFECTOR CELLS SELECTIVELY REGULATES SUSCEPTIBILITY TO CELL DEATH," *Nat. Immunol.*, 8:825-34 (2007)), a modification that involves α(2,6) sialyltransferase (ST6) and thereby prevents Gal-1 binding by masking galactose residues on LacNAc units. The anti-inflammatory activity of Gal-1 is not limited to T-cell apoptosis; it has also been found to promote differentiation of tolerogenic dendritic cells (Ilarregui et al., "TOLEROGENIC SIGNALS DELIVERED BY DENDRITIC CELLS TO T CELLS THROUGH A GALECTIN-1-DRIVEN IMMUNOREGULATORY CIRCUIT INVOLVING INTERLEUKIN 27 AND INTERLEUKIN 10," *Nat. Immunol.*, 10:981-991 (2009)), and to favor conversion of macrophages toward a M2-type phenotype (Starossom et al., "GAL-1 DEACTIVATES CLASSICALLY ACTIVATED MICROGLIA AND PROTECTS FROM INFLAMMATION-INDUCED NEURODEGENERATION," *Immunity*, 37(2):249-63 (2002)). In fact, administration of recombinant Gal-1 has been found to ameliorate disease severity in several autoimmune models of arthritis, uveitis, and TNBS-induced colitis. See Toscano et al., *Journal of Immunology*, 176:6323-32 (2006); and Santucci et al., "GALECTIN-1 SUPPRESSES EXPERIMENTAL COLITIS IN MICE," *Gastroenterology*, 124 (5): 1381-94 (2003).

The therapeutic potential of Gal-1 is, however, limited by intrinsic biochemical factors, including its sensitivity to oxidation and acidic pH, both of which are conditions typically involved in inflammatory microenvironments. Moreover, as most studies to date regarding Gal-1 function have been performed at normal physiological conditions (i.e., a pH of about 7.4), most of the available physicochemical data characterizing activity and affinity of Gal-1 does not reflect its role in an inflammatory locus where extracellular acidosis can make the pH fall below 5.5. This high proton concentration is normally attributed to infiltration and activation of inflammatory cells, leading to increased oxygen demand and energy, accelerated glycolysis, and increased lactic acid secretion. Menkin, *Science* (1956). Furthermore, although lactic acid (i.e., extracellular acidosis) has been shown to influence many processes related to the immune metabolism ((Geffner et al., (1993); Jancic et al., (2012); Kraus & Wolf, (1996); Martinez et al., (2007); Trevani et al., (1999); Vermeulen et al., (2004)), little is known about the mechanisms by which cell communication is influenced by these conditions.

It is therefore an object of the invention to investigate the effect of altered extracellular pH, particularly that of an acidic microenvironment, on immune cells and their function. More specifically, it is an object of the invention to investigate how Gal-1 affects immune cells and their function.

SUMMARY OF THE INVENTION

This Summary is provided to introduce a selection of concepts that are further described herein with respect to various embodiments of the invention. This Summary is not intended to identify key or essential features of the invention, nor is it intended to limit the scope of the invention.

The present disclosure generally relates to novel Gal-1 polypeptide variants that are resistant to unfavorable conditions typically found in inflammatory microenvironments that otherwise result in deactivation of native human Gal-1. Specifically, provided are novel rationally designed Gal-1 polypeptide variants or mutants having certain amino acid modifications that confer resistance against the observed acidic and oxidative inactivation of native human Gal-1. By eliminating the susceptibility to inactivation in inflammatory microenvironments, the novel Gal-1 variants may be used in various methods of the invention as highly effective immunomodulation agents.

Embodiments of the invention relate to Gal-1 polypeptide variants resistant to acidic conditions that otherwise result in deactivation of native human Gal-1, the Gal-1 polypeptide variants comprising a mutation of the histidine residue corresponding to position 52 of the full-length amino acid sequence of native human Gal-1 as shown in SEQ ID NO: 1, the mutation being a substitution of the histidine to tyrosine or asparagine. The polypeptide variants are resistant to acidic conditions that generally result in an extracellular pH falling below 7.0.

In certain embodiments, the Gal-1 polypeptide variants may include an additional mutation of the cysteine residue corresponding to a position selected from 2, 16, 88, or combinations thereof, of the full-length amino acid sequence of native human Gal-1 as shown in SEQ ID NO: 1, this additional mutation being a substitution of at least one cysteine to serine. Specifically, the Gal-1 polypeptide variants may include one or more additional mutation(s) of the cysteine residue, such as mutations corresponding to positions 2 and 16, or 2 and 88, of the full-length amino acid sequence of native human Gal-1 as shown in SEQ ID NO: 1. Such mutants exhibit resistance to acidic as well as oxidative conditions of an inflammatory microenvironment that otherwise results in deactivation of native human Gal-1.

In certain embodiments, the polypeptide variants include: (a) a mutation corresponding to position 52 of the full-length amino acid sequence of native human Gal-1 as shown by SEQ ID NO: 1, wherein the mutation is a substitution of the histidine to tyrosine or asparagine; and (b) a mutation of the cysteine residue corresponding to positions 2 and 16 of the full-length amino acid sequence of native human Gal-1. Such polypeptide variants exhibit a synergistic effect at physiological pH conditions with respect to resistance to both acidic and oxidative conditions, as well as pro-apoptotic activity, as compared to native human Gal-1. The polypeptide variants may furthermore induce secretion of IL-10 that is about, or at least, 16 times higher than secretion of IL-10 induced by native human Gal-1.

Embodiments of the invention also relate to nucleic acids that encode a Gal-1 polypeptide variant having a mutation corresponding to position 52 of the full-length amino acid sequence of native human Gal-1 as shown by SEQ ID NO:1, wherein the mutation is a substitution of the histidine to tyrosine or asparagine. In certain embodiments, nucleic acids described herein encode a Gal-1 polypeptide variant having: (a) a mutation corresponding to position 52 of the full-length amino acid sequence of native human Gal-1 as shown by SEQ ID NO: 1, wherein the mutation is a substitution of the histidine to tyrosine or asparagine; and (b) at least one further mutation of the cysteine residue corresponding to positions 2, 16, 88, or combinations thereof, of the full-length amino acid sequence of native human Gal-1 as shown in SEQ ID NO: 1, wherein the mutation is a substitution of the cysteine to serine.

In further embodiments, the invention relates to pharmaceutical compositions comprising the Gal-1 polypeptide variant(s), or a fragment thereof, and a pharmaceutically acceptable carrier.

Also provided are methods for modulating an immune response that may comprise contacting an immune cell with a Gal-1 polypeptide variant as described herein, wherein the mutation on the Gal-1 polypeptide variant modulates the immune response by up-regulating binding of the Gal-1 polypeptide or a fragment thereof to its natural binding partner(s) under acidic conditions of an inflammatory microenvironment that otherwise inhibit the binding of native human Gal-1 or a fragment thereof to its natural binding partner(s). In some embodiments, the methods for modulating an immune response may comprise contacting an immune cell with the Gal-1 variant in vivo. In other embodiments, the methods for modulating an immune response may comprise contacting an immune cell with the Gal-1 variant in vitro. In various aspects, the immune cell may be an animal cell, such as, e.g., a mammalian cell, such as, e.g., a human cell.

According to various embodiments of the invention, acidic conditions of an inflammatory microenvironment refer to acidic conditions resulting in an extracellular pH falling below 6.0, such as below 5.7, or below 5.5, below 5.3, or below 5.0. Such inflammatory microenvironments typically result in acid pH conditions falling below 6.0 and oxidative conditions that reduce lactose binding of native human Gal-1.

Certain embodiments also relate to methods for treating a subject having a condition in need of down-regulation of an immune response. Specifically, methods according to embodiments of the invention may comprise administering to a subject having a condition in need of down-regulation of an immune response a therapeutically effective amount of a Gal-1 polypeptide mutant that binds to natural binding partner(s) of native human Gal-1 under inflammatory conditions, wherein the Gal-1 polypeptide variant comprises: (a) a first mutation of the histidine residue corresponding to position 52 of the full-length amino acid sequence of native human Gal-1 as shown in SEQ ID NO: 1, the mutation constituting a substitution of the histidine to tyrosine or asparagine; and (b) at least one second mutation of the cysteine residue corresponding to a position selected from 16, 88, or combinations thereof of the full-length amino acid sequence of native human Gal-1 as shown in SEQ ID NO:1, the at least one second mutation constituting a substitution of the cysteine to serine.

In treatment methods encompassed by the invention, administration of a Gal-1 polypeptide variant described herein down-regulates the immune response of the subject by inducing secretion of anti-inflammatory cytokines IL-10 and IL-27. Furthermore, administration of the Gall polypeptide variants may down-regulate the immune response of the subject by inducing apoptosis of T cells without augmenting secretion of anti-inflammatory cytokines IL-19 and IL-27.

With respect to the treatment methods described herein, the subject may be a human and the condition may be an immune disorder selected from the group consisting of acute or chronic inflammatory disease, auto-immune disease, allergic disorder, arthritis, hepatitis, asthma, multiple sclerosis, transplant rejection, graft-versus-host disease (GVHD), inflammatory bowel diseases, Parkinson's disease, Alzheimer's disease, and any organ-specific autoimmune disease. In some embodiments, the Gal-1 polypeptide variant may be administered to a subject in a pharmaceutical composition that comprises the Gal-1 variant in a therapeutically effective amount, and a pharmaceutically acceptable carrier. I The pharmaceutical compositions described herein may be administered to the subject in a dosage form selected from the group consisting of tablets, capsules, pills, powders, granules, parenteral solutions or suspensions, oral solutions or suspensions, oil-water emulsions, intravenous injections, and gene therapy.

These and other features, aspects, and advantages of the invention will become better understood with reference to the following description, examples, figures, and appended claims.

BRIEF DESCRIPTION OF THE DRAWINGS

The manner in which objectives of the present disclosure and other desirable characteristics may be obtained will become further evident from the following descriptions of the appended drawings.

FIG. 3A shows the rate constants for the most reactive thiol in Gal-1, determined by plotting the determined pseudo-first-order rate constants (k') as a function of $H_2O_2$ concentration. In determining the pseudo-first-order rate constants, Gal-1 (67 μM) was incubated with $H_2O_2$ at concentrations of 2.81 mM (squares), 4.65 mM (circles), 5.56 mM (triangles), and 8.28 mM (diamonds) in PBS at 25° C. FIG. 3B shows the non-reducing and reducing SDS-PAGE results of aliquots removed from the reaction of Gal-1 with 10 mM $H_2O_2$ (ME: 2-mercaptoethanol). FIG. 3C shows the non-reducing and reducing SDS-PAGE results of WT Gal-1, C2S mutants, and C130S mutants subjected to 10 mM $H_2O_2$ oxidation for 2 hours, to which iodoacetamide (IAM) was added after $H_2O_2$ treatment to further analyze the effect of sample manipulation in free thiol oxidation after ceasing the reaction. FIG. 3D shows intensity of the emission spectrum at 363 nm, recorded and fitted as a function of lactose, of reduced (squares) and oxidized (circles) Gal-1 (8 μM) titrated by adding 100 mM lactose. FIG. 3E shows percentage of cell death observed for each recombinant Gal-1 tested (WT, CSX, and two double CSX mutants), with reduced form shown by black bars and oxidized form shown by grey bars. The results shown are representative of three independent experiments (mean±SD; *P<0.05).

FIG. 8A shows far-UV circular dichroism spectrum of a solution of WT Gal-1 and H52N, H52Y, SG1, SG2, SG3, or SG4 mutants under reducing conditions, and FIG. 8B shows the far-UV circular dichroism spectrum of these solutions after 5 days of exposure to air, with the ellipticity parameter being plotted as a function of excitation wavelength ($\lambda$ in nm). In FIG. 8D, *** indicates that the line slope that fits the WT is significantly different from zero (p<0.001).

DETAILED DESCRIPTION

A. Abbreviations & Definitions

Figure 1:
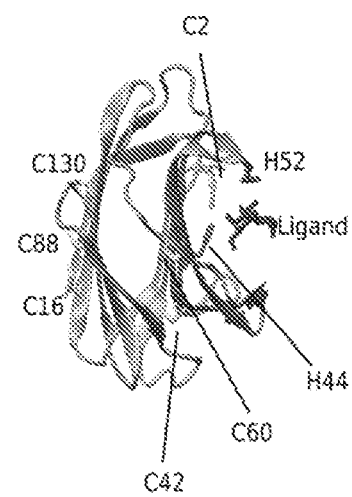
FIG. 1A shows the amino acid sequence of human Gal-1 (corresponding to SEQ ID NO: 1), with secondary annotations and numbering below the sequence corresponding to the residues of Gal-1, and the arrows representing β-strands. In the primary sequence, histidine residues are highlighted in yellow greyscales and cysteine residues are highlighted in red greyscales.
FIG. 1B shows the spatial distribution of the cysteine and histidine residues in the monomer structure of Gal-1.

The following definitions of various terms used herein are provided to facilitate understanding of the invention.

The abbreviation "CD" stands for Circular Dichroism.

The abbreviation "CRD" stands for Carbohydrate Recognition Domain.

The abbreviation "CXS" stands for Serine-to-Cysteine Gal-1 variants.

The abbreviation "DTPA" stands for Diethylene Triamine Pentaacetic Acid.

The abbreviation "EAE" stands for Experimental Autoimmune Encephalomyelitis.

The abbreviation "Gal-1" stands for Galectin-1.

The abbreviation "IAM" stands for Iodoacetamide.

The abbreviation "PBS" stands for Phosphate-Buffered Saline.

The abbreviation "SDS" stands for Sodium Dodecyl Sulfate.

The abbreviation "SDS-PAGE" stands for Sodium Dodecyl Sulfate-Polyacrylamide Gel Electrophoresis.

When introducing elements of various embodiments, the articles "a," "an," "the" and "said" are intended to mean that there are one or more of the elements. The terms "comprising," "including" and "having" are intended to be inclusive and mean that there may be additional elements other than the listed elements.

The terms "Galectin-1" or "Gal-1" as used herein refer to known Gal-1 sequences, domains, polypeptides, fragments, and variants thereof, as well as gene products of the Gal-1 gene and/or modulators thereof. Specifically, unless described otherwise (e.g., the terms being used in reference to a "variant" or "mutant" of Gal-1), the terms refer to native Gal-1. Sequences, structures, domains, and certain biophysical characteristics and functions of Gal-1 genes and gene products have been described in the art. See, e.g., Rabinovich et al., *Trends Immunol.* 23:313-320 (2002); Liu and Rabinovich, *Nature Reviews Cancer* 5:29-41 (2005); Rubinstein et al., *Cancer Cell* 5:241-251 (2004); Le et al., *J. Clin. Oncol.* 23:8932-8941 (2005); Vasta et al., *Curr. Opin. Struct. Biol.* 14:617-630 (2004); Toscano et al., *Cyt. Growth Fact. Rev.* 18:57-71 (2007); Camby et al., *Glycobiology* 16:137R-157R (2006) (the disclosures of the cited reference being incorporated by reference herein in their entireties). The Gal-1 gene is also expressed in other cells known in the art. See, e.g., Gottschalk et al., *Annu. Rev. Med.* 56, 29-44 (2005); Nalesnik et al., *Clin. Transplant.* 13, 39-44 (1999); Toscano et al., *Nat. Immunol.* 8, 825-834 (2007); Ilarregui et al., *Nat. Immunol.* 10: 981-91 (2009); Re et al., *J. Clin. Oncol.* 23, 6379-6386 (2005); Marshall et al., *Blood* 103, 1755-1762 (2004); Gandhi et al., *Blood* 108, 2280-2289 (2006); Juszczynski et al., *Proc. Natl. Acad. Sci. U.S.A.* 104, 13134-13139 (2007); Rodig et al., *Clin. Cancer Res.* 14, 3338-3344 (2008); Rabinovich et al., *Trends Immunol.* 23:313-320 (2002); Liu and Rabinovich, *Nature Reviews Cancer* 5:29-41 (2005); Rubinstein et al., *Cancer Cell* 5:241-251 (2004); Le et al., *J. Clin. Oncol.* 23:8932-8941 (2005); Vasta et al., *Curr. Opin. Struct. Biol.* 14:617-630 (2004); Toscano et al., *Cyt. Growth Fact. Rev.* 18:57-71 (2007); Camby et al., *Glycobiology* 16:137 R-157R (2006). Native human Gal-1 sequences include those provided below and in the appended Sequence Listing.

Protein Sequence of Native Human Gal-1 (SEQ ID NO: 1)

```
ACGLVASNLNLKPGECLRVRGEVAPDAKSFVLNLGKDSNNLCLHFNPRFN

AHGDANTIVCNSKDGGAWGTEQREAVFPFQPGSVAEVCITFDQANLTVKL

PDGYEFKFPNRLNLEAINYMAADGDFKIKCVAFD
```

Nucleotide Sequence of Native Human Gal-1 (SEQ ID NO: 2)

```
ATGGCTTGTGGTCTGGTCGCCAGCAACCTGAATCTCAAACCTGGAGAGTG

CCTTCGAGTGCGAGGCGAGGTGGCTCCTGACGCTAAGAGCTTCGTGCTGA

ACCTGGGCAAAGACAGCAACAACCTGTGCCTGCACTTCAACCCTCGCTTC

AACGCCCACGGCGACGCCAACACCATCGTGTGCAACAGCAAGGACGGCGG

GGCCTGGGGGACCGAGCAGCGGGAGGCTGTCTTTCCCTTCCAGCCTGGAA

GTGTTGCAGAGGTGTGCATCACCTTCGACCAGGCCAACCTGACCGTCAAG

CTGCCAGATGGATACGAATTCAAGTTCCCCAACCGCCTCAACCTGGAGGC

CATCAACTACATGGCAGCTGACGGTGACTTCAAGATCAAATGTGTGGCCT

TTGACTGA
```

The term "dosage unit form" refers to physically discrete units suited as unitary dosages for the subjects to be treated; each unit containing a predetermined quantity of active compound calculated to produce the desired therapeutic effect in association with the required pharmaceutical carrier.

As used herein, "homologs" are defined herein as two nucleic acids or peptides that have similar, or substantially identical, nucleic acids or amino acid sequences, respectively. The term "homolog" further encompasses nucleic acid molecules that differ from one of the nucleotide sequences due to degeneracy of the genetic code and thus encodes the same amino acid sequences. In one of the preferred embodiments, homologs include allelic variants, orthologs, paralogs, agonists, and antagonists of nucleic acids encoding the peptide, or analogs thereof, of the present invention. As used herein, the term "orthologs" refers to two nucleic acids from different species, but that have evolved from a common ancestral gene by speciation. Normally, orthologs encode peptides having the same or similar functions. In particular, orthologs of the invention will generally exhibit at least 80-85%, more preferably 85-90% or 90-95%, and most preferably 95%, 96%, 97%, 98%, or even 99% identity, or 100% sequence identity, with all or part of the amino acid sequence of the Gal-1 mutant polypeptides, or analogs thereof, of the present invention, preferably, SEQ ID NO:1, or mutants or variants thereof, and will exhibit a function similar to the Gal-1 mutant polypeptides. As also used herein, the term "paralogs" refers to two nucleic acids that are related by duplication within a genome. Paralogs usually have different functions, but these functions may be related.

The "percent identity" between two sequences is a function of the number of identical positions shared by the sequences (i.e., % identity=# of identical positions/total # of positions×100), taking into account the number of gaps and the length of each gap that needs to be introduced for optimal alignment of the two sequences. The comparison of sequences and determination of percent identity between two sequences can be accomplished using a mathematical algorithm, as described in the non-limiting examples below. To determine the percent sequence identity of two amino acid sequences (e.g., SEQ ID NO:1, and a mutant form thereof), the sequences are aligned for optimal comparison purposes (e.g., gaps can be introduced in the sequence of one polypeptide for optimal alignment with the other polypeptide or nucleic acid). The amino acid residues at corresponding amino acid positions are then compared. When a position in one sequence (e.g., SEQ ID NO:1) is occupied by the same amino acid residue as the corresponding position in the other sequence (e.g., a mutant form of the sequence selected from the peptide sequences of SEQ ID NO:1), then the molecules are identical at that position. The same type of comparison can be made between two nucleic acid sequences.

The determination of the percent sequence identity between two nucleic acid or peptide sequences is well known in the art. For instance, the Vector NTI 6.0 (PC)

software package (InforMax, 7600 Wisconsin Ave., Bethesda, Md. 20814) to determine the percent sequence identity between two nucleic acid or peptide sequences can be used. In this method, a gap opening penalty of 15 and a gap extension penalty of 6.66 are used for determining the percent identity of two nucleic acids. A gap opening penalty of 10 and a gap extension penalty of 0.1 are used for determining the percent identity of two polypeptides. All other parameters are set at the default settings. For purposes of a multiple alignment (Clustal W algorithm), the gap opening penalty is 10, and the gap extension penalty is 0.05 with blosum62 matrix. It is to be understood that for the purposes of determining sequence identity when comparing a DNA sequence to an RNA sequence, a thymidine nucleotide is equivalent to a uracil nucleotide.

The percent sequence identity between the two sequences is a function of the number of identical positions shared by the sequences (i.e., percent sequence identity=numbers of identical positions/total numbers of positions×100). Preferably, the isolated amino acid or nucleic acid homologs included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid or nucleic acid sequence of the aforementioned Gal-1 native human domain (SEQ ID NO: 1 and SEQ ID NO: 2). In one preferred embodiment, the isolated nucleic acid homologs of the present invention encode a mutant Gal-1 polypeptide domain comprising an amino acids sequence that is at least 90%, more preferably at least 95%, identical to an amino acid sequence of SEQ ID NO:1, and modulates down-regulation of the immune response.

As used herein, the term "inhibit" includes the decrease, limitation, or blockage, of, e.g., a particular action, function, or interaction.

As used herein, the term "modulate" includes up-regulation and down-regulation, e.g., enhancing or inhibiting a response. For example, down-regulating an immune response as described herein may include inducing secretion of anti-inflammatory cytokines (IL-10 and IL-27) with or without induction of apoptosis, and/or induction of apoptosis (T cell death) without augmentation of anti-inflammatory cytokines (IL-10 and IL-27).

As used herein, the term "nucleic acid" is intended to include DNA molecules and RNA molecules. A nucleic acid molecule may be single-stranded or double-stranded, but preferably is double-stranded DNA. As used herein, the term nucleic acid molecule is intended to include DNA molecules (e.g., cDNA or genomic DNA) and RNA molecules (e.g., mRNA) and analogs of the DNA or RNA generated using nucleotide analogs.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. In some embodiments an "isolated" nucleic acid molecule is free of sequences which naturally flank the nucleic acid (i.e., sequences located at the 5' and 3' ends of the nucleic acid molecule) in the genomic DNA of the organism from which the nucleic acid is derived. For example, an "isolated" nucleic acid molecule, such as a cDNA molecule, can be substantially free of other cellular material, or culture medium, when produced by recombinant techniques, or substantially free of chemical precursors or other chemicals when chemically synthesized. In embodiments, a nucleic acid molecule can be amplified using cDNA, mRNA or, alternatively, genomic DNA as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to nucleic acid sequences can be prepared by standard synthetic techniques, e.g., using an automated DNA synthesizer.

The term "pharmaceutically acceptable" means having been approved by a regulatory agency of the Federal or a state government or listed in the U.S. Pharmacopeia or other another generally recognized pharmacopeia for use in animals, and more particularly for use in humans.

The term "polypeptide fragment" refers to a polypeptide in which amino acid residues are deleted as compared to the reference polypeptide itself, but in which the remaining amino acid sequence is usually identical as to corresponding positions in the reference polypeptide. Such deletions may occur at one or more of the amino-terminus, internally, or at the carboxy-terminus of the reference polypeptide. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long. They can be, for example, at least and/or including 10, 15, 20, 25, 30, 35, 40, 45, 50, 55, 60, 65, 70, 75, 80, 85, 90, 95, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 720, 740, 760, 780, 800, 820, 840, 860, 880, 900, 920, 940, 960, 980, 1000, 1020, 1040, 1060, 1080, 1100, 1120, 1140, 1160, 1180, 1200, 1220, 1240, 1260, 1280, 1300, 1320, 1340 or more long so long as they are less than the length of the full-length polypeptide. Alternatively, they can be no longer than and/or excluding such a range so long as they are less than the length of the full-length polypeptide. A fragment can retain one or more of the biological activities of the reference polypeptide. In various embodiments, a fragment may comprise an enzymatic activity and/or an interaction site of the reference polypeptide, and also may have immunogenic properties.

The term "probe" refers to any molecule that is capable of selectively binding to a specifically intended target molecule, for example, a nucleotide transcript or protein encoded by or corresponding to a marker. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and other organic molecules.

As used herein, "subject" refers to any healthy animal, such as a mammal (e.g., human) or any animal afflicted with a disease or condition that would benefit from up-regulation of an immune response. The term "subject" is interchangeable with "patient."

As used herein, the term "therapeutically effective amount" refers to amounts that, when administered to a particular subject in view of the nature and severity of that subject's disease or condition, will have a desired therapeutic effect, e.g., an amount that will cure, prevent, inhibit, or at least partially arrest or relieve a target disease or condition.

As used herein, "administering" refers to various means of introducing a target composition (specifically, a Gal-1 variant according to the invention) to a cell or tissue, or to a patient. These means are commonly known in the art, include those specifically discussed herein.

A "transcribed polynucleotide" or "nucleotide transcript" is a polynucleotide (e.g., an mRNA, hnRNA, a cDNA, or an analog of such RNA or cDNA) that is complementary to or homologous with all or a portion of a mature mRNA, made by transcription of a marker and post-transcriptional processing (e.g., splicing), if any, of the RNA transcript, and reverse transcription of the RNA transcript.

As used herein, the term "T cell" includes CD4+ T cells and CD8+ T cells. The term T cell also includes both T helper 1 type T cells and T helper 2 type T cells. The term "antigen presenting cell" includes professional antigen presenting cells (e.g., B lymphocytes, monocytes, dendritic cells, Langerhans cells) as well as other antigen presenting cells (e.g., keratinocytes, endothelial cells, astrocytes, fibroblasts, oligodendrocytes).

As used herein, the terms "treat" or "treatment" refer to relief from, or alleviation of pathological processes mediated by Gal-1 binding and expression. In the context of the present invention, the terms mean to relieve or alleviate at least one symptom associated with a condition or disease that would benefit from down-regulation of an immune response, or to slow or reverse the progression of such condition or disease.

As used herein, the term "vector" refers to a nucleic acid capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors." In general, expression vectors of utility in recombinant DNA techniques are often in the form of plasmids. The terms "plasmid" and "vector" may be used interchangeably, as the plasmid is the most commonly used form of a vector. However, the disclosure is intended to also include other forms of expression vectors that serve similar functions, such as, e.g., as viral vectors.

B. Discussion

By analyzing key characteristics of Gal-1 inactivation, the presently named inventors have demonstrated that low pH and redox microenvironmental factors play a role in disrupting Gal-1 function. Specifically, a detailed study was undertaken analyzing key characteristics of the inactivation of Gal-1 due to oxidation, and further implications on immunosuppressive effects. Guardia et al., "STRUCTURAL BASIS OF REDOX-DEPENDENT MODULATION OF GAL-1 DYNAMICS AND FUNCTION," *Glycobiology*, 24(5):428-41 (2014) (incorporated by reference herein in its entirety). Results of the study established that Gal-1 activity is dependent on the oxidation of certain cysteine residues present in each carbohydrate recognition domain (CRD) of Gal-1, as redox environmental conditions were found to inhibit lactose binding and diminish apoptosis of T cell lines. A discussion of this detailed study, as well as Gal-1 polypeptide variants having resistance to oxidative conditions that were generated as a result of the study, is provided herein as Example 1.

As an objective of the present invention, a further study was undertaken to evaluate the effects of acidosis on Gal-1 structure and function. A discussion of the experiments evidencing how acidity hampers the anti-inflammatory activity of the glycan-binding Gal-1 protein and its intrinsic structural causes is provided herein as Example 2.

Based on observations that adverse conditions of inflammatory microenvironments (i.e. low pH and oxidative conditions) lead to Gal-1 inactivation, a further objective of the invention was to provide lectin variants suitable for therapeutic that could overcome overcome the aforementioned limitations by eliminating sensitivity to oxidation and acidic pH.

Employing the observations from the respective studies, a further objective achieved by the present invention was the generation of rationally designed Gal-1 polypeptide variants ("SuperGal variants") having certain amino acid modifications that provide a solution for the observed acidic and oxidative deactivations of native human Gal-1. As discussed herein and in the Examples below, variants were generated by site-directed mutagenesis, replacing His52 for asparagine or tyrosine, as well as variants resistant to oxidation by replacing cysteine residues with serines. Then, the combination of both types of mutations resulted in a number of variants, called "SuperGals" (SGs), which not only showed resistance to both oxidation and acidic pH, but also showed a significantly enhanced immunoregulatory activity (T cell apoptosis and secretion of tolerogenic/immunosuppressive cytokines). In vivo results further demonstrated applicability of these SuperGal variants, and particularly SG2, as therapeutic agents for treatment and prophylaxis of autoimmune diseases.

Specifically, as further discussed in Example 3 of the disclosure, eliminating susceptibility to inflammatory microenvironments, the novel Gal-1 polypeptide variants serve as robust immunomodulation agents, offering a promising option for autoimmune disease treatments. Based on the observations described with respect to Examples 1-3 and the supporting data presented in the appended figures, the mutations H52, C2, C16 and/or C88 of the novel Gal-1 variants provide resistance to acidic pH and oxidative conditions that otherwise result in deactivation of native human Gal-1, or inhibit immune regulation of native human Gal-1.

Therefore, the present disclosure generally relates to novel Gal-1 variants that are resistant to unfavorable conditions typically found in inflammatory microenvironments that otherwise result in deactivation of native human Gal-1. Specifically, provided are novel rationally designed Gal-1 variants having certain amino acid modifications that confer resistance against the observed acidic and oxidative inactivation of native human Gal-1. By eliminating the susceptibility to inflammatory microenvironments, the novel Gal-1 variants may be used in methods of the invention as highly effective immunomodulation agents.

In certain embodiments, the invention relates to Gal-1 variants resistant to acidic conditions that otherwise result in deactivation of native human Gal-1, the Gal-1 variants comprising a Gal-1 polypeptide having a mutation of the histidine residue corresponding to position 52 of the full-length amino acid sequence of native human Gal-1 as shown in SEQ ID NO: 1, the mutation being a substitution of the histidine to tyrosine or asparagine.

In certain embodiments, the Gal-1 variants may include a further mutation of the cysteine residue corresponding to a position selected from 2, 16, 88, or combinations thereof of the full-length amino acid sequence of native human Gal-1 as shown in SEQ ID NO: 1, the further mutation being a substitution of at least one cysteine to serine. Specifically, the Gal-1 variants may include one or more further mutation(s) of the cysteine residue, such as mutations corresponding to positions 2 and 16 or 2 and 88 of the full-length amino acid sequence of native human Gal-1 as shown in SEQ ID NO: 1. Such mutants exhibit resistance to acidic as well as oxidative conditions of an inflammatory microenvironment that otherwise result in deactivation of native human Gal-1.

In embodiments, the Gal-1 variants comprise a Gal-1 polypeptide having at least 80% sequence homology, such as at least 85%, at least 90%, at least 95%, at least 96%, at least 97%, at least 98%, or at least 99% sequence homology with the full-length amino acid sequence of native human Gal-1.

Embodiments of the invention also relate to nucleic acids that encode a Gal-1 polypeptide having a mutation corresponding to position 52 of the full-length amino acid sequence of native human Gal-1 as shown by SEQ ID NO: 1, wherein the mutation is a substitution of the histidine to tyrosine or asparagine. In certain embodiments, nucleic acids described herein encode a Gal-1 polypeptide having: (a) a mutation corresponding to position 52 of the full-length amino acid sequence of native human Gal-1 as shown by SEQ ID NO: 1, wherein the mutation is a substitution of the histidine to tyrosine or asparagine; and (b) at least one further mutation of the cysteine residue corresponding to positions 2, 16, 88, or combinations thereof of the full-length amino acid sequence of native human Gal-1 as shown in SEQ ID NO: 1, wherein the mutation is a substitution of the cysteine to serine.

Embodiments of the invention also relate to pharmaceutical compositions comprising a Gal-1 polypeptide variant of the invention, or a fragment thereof, and a pharmaceutically acceptable carrier.

A pharmaceutically acceptable carrier for use in the pharmaceutical compositions may include a diluent, adjuvant, excipient, or vehicle with which a compound, such as the Gal-1 variant, may be administered. Such carriers can be sterile liquids (such as, e.g., water and oils), including those of petroleum, animal, vegetable, or synthetic origin (such as, e.g., peanut oil, soybean oil, mineral oil, sesame oil, and the like); polyethylene glycols; glycerine; propylene glycol; and other synthetic solvents. Water is a preferred carrier when a compound is administered intravenously. Saline solutions and aqueous dextrose and glycerol solutions may also be employed as liquid carriers, particularly for injectable solutions.

Suitable excipients for use as carriers include starch, sucrose, gelatin, rice, flour, chalk, silica gel, sodium stearate, glycerol monostearate, talc, sodium chloride, glycerol, propylene, glycol, water, ethanol, and the like. A compound or composition, if desired, can also combine minor amounts of wetting or emulsifying agents, or pH buffering agents, such as acetates, citrates, or phosphates, antibacterial agents, such as benzyl alcohol or methyl parabens; antioxidants, such as ascorbic acid or sedum bisulfite; chelating agents, such as ethylenediaminetetraacetic acid; and agents for the adjustment of toxicity, such as sodium chloride or dextrose, may also be used as a carrier. Methods for producing compounds or compositions with carriers are conventionally known to persons skilled in the art.

In embodiments, a pharmaceutical composition may be formulated to be compatible with its intended route of administration. Administration of the composition according to embodiments of the invention may include (but are not limited to) oral (e.g., inhalation), subcutaneous, parenteral, intraocular, intradermal, intramuscular, intraperitoneal, intratracheal, sublingual, topical, buccal, rectal, vaginal, and topical.

Pharmaceutical compositions suitable for injectable use generally include sterile aqueous solutions (where water soluble) or dispersions and sterile powders for the extemporaneous preparation of sterile injectable solutions or dispersion. In all cases, the composition should be sterile and should be fluid to the extent that easy syringeability exists. Sterile injectable solutions can be prepared by incorporating the active ingredient (one of the Gal-1 variants described herein) in the required amount in an appropriate solvent with one or a combination of ingredients enumerated above, followed by filtered sterilization. Oral compositions generally include an inert diluent or an edible carrier. For the purpose of oral therapeutic administration, the active ingredient can be incorporated with excipients and used in the form of, e.g., tablets or capsules. Oral compositions may also be prepared using a fluid carrier for use as a mouthwash, wherein the active compound in the fluid carrier is applied orally and swished and expectorated or swallowed. For administration by inhalation, the Gal-1 variants may be delivered in the form of an aerosol spray from a pressured container or dispenser. Systemic administration of the pharmaceutical compositions may also be by transmucosal or transdermal means, where transmucosal administration can be accomplished through the use of, e.g., a nasal spray or suppository, and transdermal administration can be accomplished by formulating the active compound into ointments, salves, gels, or creams.

Also provided are methods for modulating an immune response that may comprise contacting an immune cell with a Gal-1 variant (or "SuperGal") described herein, wherein the Gal-1 variant modulates the immune response by up-regulating binding of the Gal-1 polypeptide or a fragment thereof to its natural binding partner(s) under acidic conditions of an inflammatory microenvironment that otherwise inhibit the binding of native human Gal-1 or a fragment thereof to its natural binding partner(s). In embodiments, acidic conditions of an inflammatory microenvironment refer to acidic conditions resulting in an extracellular pH falling below 6.0, in some embodiments falling below 5.5, such as below 5.3, or below 5.0, and oxidative conditions of an inflammatory microenvironment that reduce lactose binding of native human Gal-1.

In the methods for modulating an immune response, the Gal-1 variants may be administered as modulating agents, e.g., in the form of small molecules. Such small molecules include, but are not limited to, peptides, peptidomimetics, amino acids, amino acid analogs, polynucleotides, polynucleotide analogs, nucleotides, nucleotide analogs, organic or inorganic compounds (i.e., including hetero-organic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the scope of knowledge of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the present disclosure, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

In the methods for modulating an immune response, contacting of the immune cell with the Gal-1 polypeptide variant may occur in vivo or in vitro. In various aspects, the immune cell may be an animal cell, such as, e.g., a mammalian cell, such as, e.g., a human cell.

In embodiments, the Gal-1 variants may be administered as modulatory agents that modulate an immune response and are prepared with carriers that will protect the active compound against rapid elimination from the body, such as a controlled release formulation, including implants and microencapsulated delivery systems.

Certain embodiments also relate to methods for treating a subject having a condition in need of down-regulation of an immune response. Specifically, methods according to various embodiments of the invention may comprise administering to a subject having a condition in need of down-regulation of an immune response a therapeutically effective amount of a Gal-1 variant that binds to natural binding partner(s) of native human Gal-1 under inflammatory conditions, wherein the Gal-1 polypeptide variant comprises: (a) a first mutation of the histidine residue corresponding to position 52 of the full-length amino acid sequence of native human Gal-1 as shown in SEQ ID NO: 1 the mutation constituting a substitution of the histidine to tyrosine or asparagine; and (b) at least one second mutation of the cysteine residue corresponding to a position selected from 2, 16, 88, or combinations thereof of the full-length amino acid sequence of native human Gal-1 as shown in SEQ ID NO: 1, the at least one second mutation constituting a substitution of the cysteine to serine.

With respect to the treatment methods described herein, the subject may be a human and the condition may be an immune disorder selected from the group consisting of acute or chronic inflammatory disease, auto-immune disease, allergic disorder, arthritis, hepatitis, asthma, multiple sclerosis, transplant rejection, graft-versus-host disease (GVHD), inflammatory bowel diseases, Parkinson's, Alzheimer's, and any organ-specific autoimmune disease.

In embodiments, the invention provides methods for treating, in a subject, a disease or condition associated with aberrant Gal-1 binding affinity to β-galactosides by administering a Gal-1 as described herein that modulates binding of the Gal-1 polypeptide to β-galactosides under acidic and oxidative conditions, wherein the disease or condition is selected from encephalomyelitis and multiple sclerosis.

In some embodiments, the Gal-1 variant may be administered to a subject in a pharmaceutical composition that comprises the Gal-1 variant in a therapeutically effective amount, and a pharmaceutically acceptable carrier. In various aspects, such pharmaceutical compositions may be administered to the subject in a dosage form selected from the group consisting of tablets, capsules, pills, powders, granules, parenteral solutions or suspensions, oral solutions or suspensions, oil-water emulsions, intravenous injections, and gene therapy.

It is typically advantageous to formulate oral or parenteral compositions in dosage unit forms for ease of administration and uniformity of dosage. The specifications for the dosage unit form are dictated by, and directly dependent on, the unique characteristics of the active compound (e.g., the specific amino acid mutation(s) of the Gal-1 mutant), the particular therapeutic effect to be achieved, and the limitations inherent in the art of compounding such active compounds for treatment of individuals.

Based in the experimental results discussed herein, the Gal-1 polypeptide variants were generated by site-directed mutagenesis on: (i) individual histidine residues in the Gal-1 native human sequence that confer sensitivity to low pH; and (ii) individual cysteine residues that are responsible for oxidative inactivation of this lectin (FIGS. 1A-1B). The results demonstrated that mutations of H52, C2, C16 and/or C88 in Gal-1 provided resistance to acidic pH and oxidative conditions. So far, combination of these mutations in mutant SG2 showed (by in vitro and in vivo assays) resistance to both conditions and an improved immunomodulatory activity. Meanwhile, SG1 exhibits an enhanced capacity to induce secretion of anti-inflammatory cytokines (IL-10 and IL-27), promoting a tolerogenic environment without induction of T cell death. SG4, on the other hand, activates T cell death programs without augmenting anti-inflammatory cytokines (IL-10 and IL-27). These different profiles of the SGXs may be further exploited therapeutically to offer different therapeutic advantages by selectively activating either one or both of these mechanisms depending on the nature of each autoimmune disease.

In summary, the present study addresses a complete scenario of the modulation of Gal-1 function by acidic or oxidative environments and its structural causes, while the robust Gal-1 variants hereby generated and described offer a promising option to treat autoimmune and inflammatory diseases.

EXAMPLES

A. Materials & Methods

All experiments were performed at 25° C. in 100 mM phosphate-buffered saline (PBS) containing 0.1 mM diethylenetriaminepentaacetic acid (DTPA), at pH 7.4, unless otherwise indicated herein.

Expression and Purification of Recombinant Gal-1 and CXS Mutants

Recombinant human Gal-1 was produced according to the procedures outlined in Pace et al., "PREPARATION OF RECOMBINANT HUMAN GALECTIN-1 AND USE IN T-CELL DEATH ASSAYS," *Methods Enzymol.* 363:499-518 (2003). A similar protocol was adopted for the production of the mutant variants. Briefly, *Escherichia coli* BL21 (DE3) cells were transformed with each plasmid containing different genes inserted into the expression vector pET22b (Novagen), and production of the recombinant galectin was induced at the log phase by addition of 1 mM isopropyl β-D-thiogalactoside. Cells were separated by centrifugation, washed and disrupted by sonication. Debris was eliminated after centrifugation at 15,000× g, and soluble fractions were obtained for subsequent purification by affinity chromatography on a lactosyl-Sepharose column, using 0.1 M lactose in PBS supplemented with 4 mM β-ME as elution buffer. Eluted Gal-1 was further purified using a HiPrep Sephacryl S-100 HR gel filtration column (GE Healthcare). After gel filtration, galectin-containing fractions were subjected to extensive dialysis against PBS containing 4 mM β-ME at 4° C. to remove lactose bound to the protein. LPS was then depleted with a Polymyxin B-Agarose column. The rGal-1 was aliquoted into suitable volumes and stored at −20° C. in PBS containing 1 mM β-ME.

Oxidants, Protein, and Thiol Quantification

In Gal-1 oxidation assays, to prevent mixed disulfide bridge formation between cysteine residues and β-ME, the β-ME was removed from the protein structure prior to any analysis by incubating the lyophilized sample in PBS with 10 mM DTT on ice during 30 min and desalting with a NAP-5 column (GE Healthcare). This procedure removes excess of DTT and β-ME. The reduced protein samples were immediately purged with argon in a closed vessel and the solution was kept on ice until use. The concentration of $H_2O_2$ (Mallinckrodt Chemicals) stock solutions was measured at 240 nm (c 240=43.6 $M^{-1}cm^{-1}$). Protein concentration after reduction treatment was measured spectrophotometrically using an absorption coefficient at 280 nm of 8480 $M^{-1}cm^{-1}$ for Gal-1 and the single cysteine mutants, as assessed from their primary sequences. Thiols were determined with 5,5'-dithiobis-(2-nitrobenzoic) acid (DTNB) after incubating Gal-1 samples with an excess of DTNB in PBS for 30 min in the dark at room temperature. An absorption coefficient at 412 nm of 14,150 $M^{-1}cm^{-1}$ (Riddles et al., "ELLMANS REAGENT—5,5-DITHIOBIS (2-NITROBENZOIC ACID)—RE-EXAMINATION," *Anal. Biochem.*, 94:75-81 (1979)) was used to quantify the 5-thio-3-nitrobenzoate anion with the absorbance of the DTNB solution and the intrinsic low absorbance of Gal-1 at this wavelength accounted for.

Generation of Gal-1 Polypeptide Variants

Two single mutants (H52Y and H52N) and four triple mutants (C2SC16SH52Y, C2SC16SH52N, C2SC88SH52Y and C2SC88SH52N) of Gal-1 were obtained using the inverse polymerase chain method as described in Clackson et al., "GENERAL APPLICATION OF PCR TO GENE CLONING AND MANIPULATION," *PCR, a practical approach; Oxford: IRL Press at* Oxford University Press (1991). The forward sense primer contained a mismatch that changed the appropriate amino acid residue. These primers were used in combination with antisense primers that start at the beginning of the sense primers, as provided in Table 1 below. The mutation H44Q was previously tested, as reported in Hiramatsu et al., "INVOLVEMENT OF HISTIDINE RESIDUES IN THE pH-DEPENDENT b-GALACTOSIDE BINDING ACTIVITY OF HUMAN GAL-1," *Biochemistry* (2013) (the disclosure of which is incorporated by reference herein in its entirety).

TABLE 1

| Mutation | Direction | Primer | |
|---|---|---|---|
| H52N | Forward | 5'-CAACGCCAACGGCGACGCCAAC-3' | (SEQ ID NO: 3) |
| H52N | Reverse | 5'-GTTGGCGTCGCCGTTGGCGTTG-3' | (SEQ ID NO: 4) |
| H52Q | Forward | 5'-CAACGCCCAGGGCGACGCCAAC-3' | (SEQ ID NO: 5) |
| H52Q | Reverse | 5'-GTTGGCGTCGCCCTGGGCGTTG-3' | (SEQ ID NO: 6) |
| H52Y | Forward | 5'-CAACGCCTATGGCGACGCCAAC-3' | (SEQ ID NO: 7) |
| H52Y | Reverse | 5'-GTTGGCGTCGCCATAGGCGTTG-3' | (SEQ ID NO: 8) |
| H44N | Forward | 5'-TGTGCCTGAACTTCAACCCTCG-3' | (SEQ ID NO: 9) |
| H44N | Reverse | 5'-CGAGGGTTGAAGTTCAGGCACA-3' | (SEQ ID NO: 10) |
| H44Y | Forward | 5 '-TGTGCCTGTACTTCAACCCTCG-3' | (SEQ ID NO: 11) |
| H44Y | Reverse | 5'-CGAGGGTTGAAGTACAGGCACA-3' | (SEQ ID NO: 12) |

The insert and the vector were amplified on the same step with KOD Hot Start polymerase (Novagen) and the resulting product was ligated with T4 DNA Ligase (Promega). Triple mutants were generated using the double mutant C2SC16S or C2SC88S as starting materials (Guardia et al., 2014) and the mutations were introduced using the primers previously employed to generate the single mutants H52Y and H52N. Mutations were checked by DNA sequencing of the entire insert. Suitable primers may include those provided in Table 2, which correspond to the primers described in Guardia et al., "STRUCTURAL BASIS OF REDOX-DEPENDENT MODULATION OF GAL-1 DYNAMICS AND FUNCTION," *Glycobiology*, 24(5):428-41 (2014) (the disclosure of which is incorporated by reference herein in its entirety).

TABLE 2

| Mutation | Direction | Primer | |
|---|---|---|---|
| C2S | Forward | 5'-ATATGGCTTCTGGTCTGG-3' | (SEQ ID NO: 13) |
| C2S | Reverse | 5'-GTATATCTCCTTCTTAAAGTTAAAC-3' | (SEQ ID NO: 14) |
| C16S | Forward | 5'-CTGGAGAGTTCCCTTCGAGTG-3' | (SEQ ID NO: 15) |

TABLE 2-continued

| Mutation | Direction | Primer | |
|---|---|---|---|
| C16S | Reverse | 5'-GTTTGAGATTCAGGTTGCTGG-3' | (SEQ ID NO: 16) |
| C42S | Forward | 5'-CAACCTTGTCCCTGCACTTC-3' | (SEQ ID NO: 17) |
| C42S | Reverse | 5'-TTGCTGTCTTTGCCCAGGTTC-3' | (SEQ ID NO: 18) |
| C60S | Forward | 5'-CCATCGTGTCCAACAGCAAG-3' | (SEQ ID NO: 19) |
| C60S | Reverse | 5'-TGTTGGCGTCGCCGTG-3' | (SEQ ID NO: 20) |
| C88S | Forward | 5'-CAGAGGTGTCCATCACCTTC-3' | (SEQ ID NO: 21) |
| C88S | Reverse | 5'-CAACACTTCCAGGCTGGAAG-3' | (SEQ ID NO: 22) |
| C130S | Forward | 5'-CAAGATCAAATCTGTGGCCTTTG-3' | (SEQ ID NO: 23) |
| C130S | Reverse | 5'-AAGTCACCGTCAGCTGC-3' | (SEQ ID NO: 24) |

Spectroscopic Measurements

Far- and near-UV CD spectra were recorded using a Jasco J-815 spectropolarimeter equipped with a Peltier temperature control. Spectra shown are averages of at least eight scans, with background corrected by the subtraction of respective buffer blanks. They were acquired over the wavelength range of 190-360 nm, using a 1 mm path length polarimetrically certified cell (Hellma). Spectra deconvolution was performed using DichroWeb with the CONTIN analysis program and the reference set SP175. Intrinsic fluorescence emission spectra were measured at 25° C. in a Jasco FP-6500 spectrofluorometer. Excitation wavelength was set to 295 nm, and spectra were recorded between 305 and 400 nm. Excitation and emission bandpasses were set to 1 and 5 nm, respectively. An average of at least six scans was used for final calculations. Spectra were corrected for dilution effects, and the final dilution of the sample was always <10%.

Binding of Gal-1 to Lactose

The Gal-1:lactose binding constant at different pH conditions (Example 2) was determined by fitting the fluorescence emission spectrum change at pH=7.5, 6.5 or 5.5, respectively. Gal-1 (5 µM) was titrated by adding aliquots of a 100 mM lactose stock solution. The intensity of the emission spectrum at 354 nm was recorded and fitted as function of lactose concentration. Binding constant ($K_b$) at 25° C. was calculated by fitting a single binding site model to the fluorescence data.

Sodium Dodecyl Sulfate-Polyacrylamide Gel Electrophoresis

Sodium dodecyl sulfate-polyacrylamide gel electrophoresis (SDS-PAGE) was performed using 15:1 polyacrylamide gels containing SDS further stained with silver or Coomassie blue.

T-Cell Death Assays

T cell lines ($5 \times 10^5$) were cultured according to procedures described in Lange et al., "GALECTIN-1 INDUCED ACTIVATION OF THE MITOCHONDRIAL APOPTOTIC PATHWAY: WAYS IN HUMAN JURKAT T LYMPHOCYTES," *Histochem. Cell Biol.*, 132:211-23 (2009)), and incubated with or without 3 µM Gal-1 or its variants in Roswell Park Memorial Institute (RPMI) medium supplemented with 5% fetal bovine serum (FBS), penicillin (100 mU/mL) and streptomycin (50 µg/mL) in 24-well culture plates at 37° C. in 5% $CO_2$. To generate reducing conditions (in Example 1), 0.55 mM ME (final concentration) was added to complete the medium before adding the cell suspension. To test the functional activity of oxidized galectins, galectins were cultured in RPMI and treated with 10 mM $H_2O_2$ for 20 minutes before the assays. The excess of ROS was quenched by using catalase (100 U/mL) and the oxidation reaction was stopped. Then, the medium was completed with FBS and antibiotics and cells were added to each well. After 14 hours of exposure to Gal-1 or its variants, cells were washed with PBS. Cell death was determined by annexin V-FITC/propidium iodide (PI) in staining buffer (100 mM HEPES, 1.4 M NaCl, 25 mM $CaCl_2$) as previously described in Toscano et al., *Nat. Immunol.*, 8:825-34 (2007). Fluorescence (FITC and PI) was analyzed with FACS Canto (BD Biosciences). Cell death was calculated as the percent of annexin V-positive cells in galectin-treated cells minus the percentage of annexin V-position control-treated cells.

Solid Phase Assays

Solid phase assays used herein were adapted from Rapaport et al. (incorporated by reference herein). First, asialofetuin (10 µg/ml) in $NaHCO_3$ buffer (pH 9.6) was coated on a 96-well microplate and incubated at 4° C. over night. Different concentrations of lactose (0.2-8 mM), in the appropriate buffer solution (pH 7.5, 6.5 or 5.5) containing BSA 0.3%, were incubated with Gal-1 (20 µg/ml, expressed recombinantly as previously described) at 37° C. for 2 hours in eppendorf tubes, and then the mixture was added into the plate wells with immobilized asialofetuin. The plate was then incubated at 37° C. for 2 hours, washed with PBS-Tween 0.05%, and further incubated with biotinilated antibodies against Gal-1 at room temperature for 1 hour. Then, the plate was washed with PBS-Tween 0.05% and incubated with streptavidin-peroxidase at room temperature for 30 minutes. After termination of reaction, the washing was repeated and Gal-1 detected with Tetramethylbenzide (TMB). The reaction must be stopped with $H_2SO_4$ 2N. Absorbance was determined at 450 nm with a spectrophotometer and fitted as a function of lactose concentration. The concentration of lactose (in µM) required for 50% inhibition (IC 50 value) was calculated by fitting the absorbance data. The individual experimental series with at least duplicates were carried out independently at least four times up to the level of saturation of binding the labeled protein in solution.

Statistical Analysis

Data are expressed as mean±SD. Prism software (GraphPad Software) was used for statistical analysis. Two groups were compared with Student's t-test for unpaired data. P-values of 0.05 or less were considered significant.

B. Example 1

Redox-Dependent Modulation of Gal-1 Function

In a prior study using a combination of in vitro and in silico experiments, the named inventors studied the molecular mechanisms underlying Gal-1 oxidation. A hierarchy based on reactivity and importance of each cysteine residue of Gal-1 was established and kinetics of oxidation with hydrogen peroxide was characterized. The first surprising result was the high degree of reversibility of the oxidation-reduction process. Since only four of the six thiols present in Gal-1 are exposed to solvent, it was postulated that the cysteine residues responsible for triggering the oxidation-driven conformational change of the protein are among these four residues.

Figure 2:
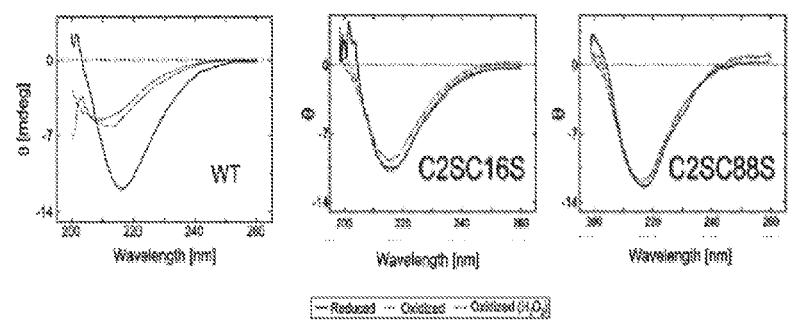
FIG. 2 shows circular dichroism (CD) spectra of different redox states of Gal-1 and CXS double mutants. All of the reduced forms of Gal-1 and its CXS double mutants (solid line) exhibited similar CD spectra, but when oxidized in air (dotted line) or with hydrogen peroxide (dot-dash line), different spectra were obtained as a function of the absence of particular cysteine residues. Of all the CXS mutants tested (not shown) only C16S and C88S mutants generated the conformation state of the oxidized form of WT Gal-1 when oxidized in air, and also kept the reduced protein conformation when hydrogen peroxide was used to induce protein oxidation.
Figure 3:
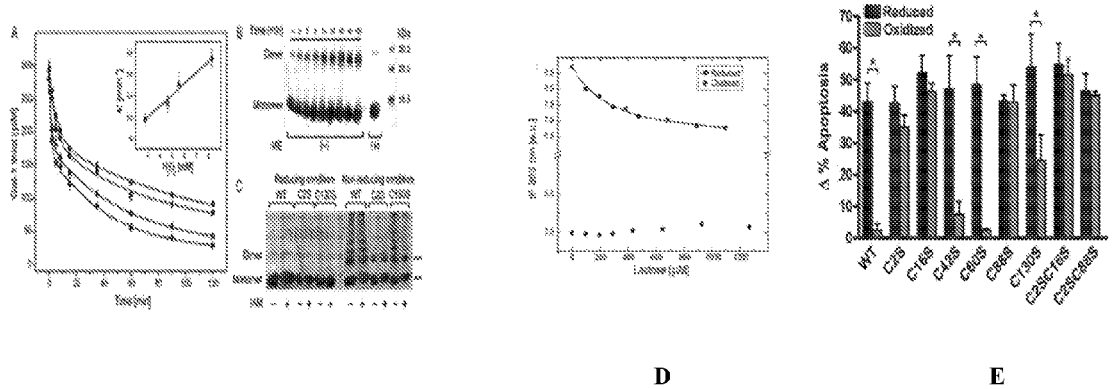
FIGS. 3A-3E show kinetics of oxidation of Gal-1 with $H_2O_2$.
Figure 4:
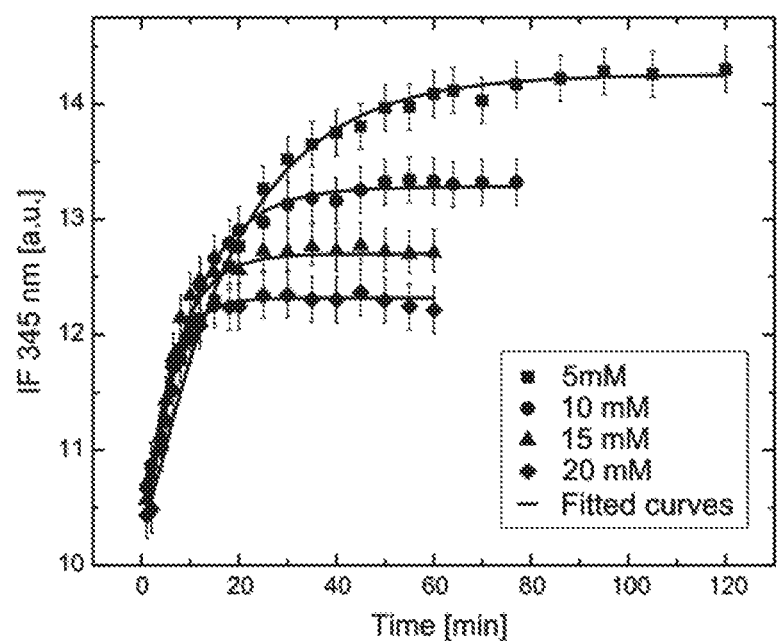
FIG. 4 shows the kinetics analysis of conformational changes of Gal-1 upon oxidation with $H_2O_2$. Gal-1 (7 μM) was incubated with hydrogen peroxide at concentrations of 5 mM (squares), 10 mM (circles), 15 mM (triangles) and 20 mM (diamonds) in PBS buffer (100 mM, 0.1 mM DTPA, pH 7.4) at 25° C., and the intensity of the emission spectrum at 345 nm was recorded as a function of time. A kinetics model taking into account the consumption of reduced Gal-1, the formation of the different oxidized Gal-1 species and the concentration of hydrogen peroxide was fitted (line) in order to obtain the rate of conformational changes and the reactions corresponding to overoxidation of cysteines.

To fully dissect the contribution of each cysteine to the oxidation process, six single cysteine mutants (CXS), as well as two selected double mutants were expressed and purified, and exposed to the same reduction and oxidation procedures previously used for WT Gal-1. The apoptotic activities of reduced or oxidized WT Gal-1 and the different Cys to Ser mutants (C2S, C16S, C42S, C60S, C88S, C130S) are shown in FIG. 2, demonstrating that only mutants C2S, C16S, and C88S (i.e., those mutants lacking Cys2, Cys16, and Cys88, respectively), elicited T cell apoptosis to the same extent as WT Gal-1 when exposed to oxidizing conditions. In addition to the CXS single mutants, two Gal-1 double mutant variants (C2S-C16S and C2S-C88S) were generated. As shown in FIG. 3, although oxidation of WT Gal-1 resulted in gradual loss of pro-apoptotic activity, the prevalent redox condition did not change the apoptotic effect on T-cells of the double mutants.

Furthermore, given their proximity and the particular acidity of one of these residues, Cys16 and Cys88 were also found to be good candidates to form a disulfide bridge, as supported by experimental evidence provided in Tracey et al., "SUBUNIT MOLECULAR MASS ASSIGNMENT OF 14,654 DA TO THE SOLUBLE BETA-GALACTOSIDE-BINDING LECTIN FROM BOVINE HEART MUSCLE AND DEMONSTRATION OF INTRAMOLECULAR DISULFIDE BONDING ASSOCIATED WITH OXIDATIVE INACTIVATION," *J. Biol. Chem.* 267: 10342-47 (1992). In this regard, the formation of three disulfide bonds, involving the conformational change induced by oxidation when Cys42, Cys60, or Cys130 were mutated indicated almost no relevance of these residues in the overall oxidation process.

In sum, results of the redox study demonstrated the following:
from the six cysteine residues present in Gal-1 (Cys2, Cys16, Cys42, Cys60, Cys88, Cys130), only three cysteine residues present in each Gal-1 carbohydrate recognition domain (Cys2, Cys16 and Cys88) are important in protein oxidation;
the oxidized Gal-1 protein did not bind to lactose, likely due to poor interactions with Arg48 and Glu71;
oxidation was found to be slow ($1.7\pm0.2$ $M^{-1}s^{-1}$ at 25° C.);
oxidation was promoted by the formation of the Cys16-Cys88 disulfide bond as well as multimers through Cys2; and
oxidation of WT Gal-1 did not trigger apoptosis of a T cell line.

C. Example 2 pH-Dependent Modulation of Gal-1 Function

T-cell death assays in the presence of Gal-1 were performed under different pH environments in order to mimic the typical acidosis found in inflammation. As previously reported (Toscano et al., *Nat. Immunol.*, 8:825-34 (2007)) and shown in FIG. 5A, human TCD4+ activated cells show susceptibility to Gal-1. However, its pro-apoptotic effect was found to be substantially affected by pH with a significant decrease in activity occurring in the range of pH 6.5 to 6.

Figure 5:
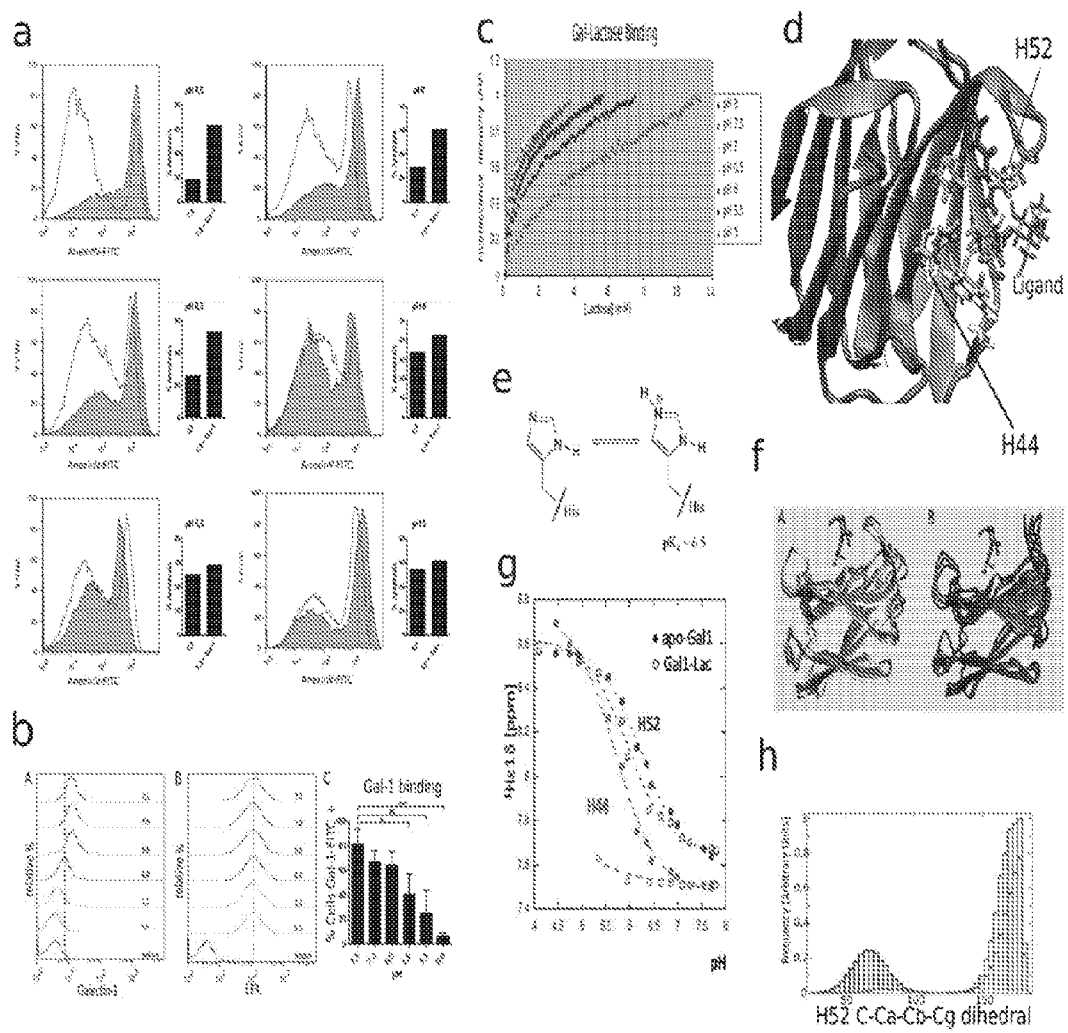
FIG. 5A shows a comparison of the apoptotic effects of recombinant Gal-1 on PBMCs under different pH environments that mimic the typical acidosis found in inflammation.
FIG. 5B shows the decreased binding capacity of Gal-1 under the various pH environments under study.
FIG. 5C shows lactose binding to Gal-1.
FIG. 5D provides a detailed view of the Gal-1 ligand binding groove, showing key amino acids interacting directly with the ligand moiety, and specifically displaying the location of histidines 44 and 52.
FIG. 5E shows the protonation equilibrium for the histidine imidazole ring.
FIG. 5F provides a detailed view as derived by MD simulations of both Gal-1 with Histidine 52 in a double-protonated state and in a mono-protonated state, respectively.
FIG. 5G shows the calculated pKa values, plotted as a function of pH, for the histidine residues in mono- and di-protonated states, respectively.
FIG. 5H shows orientation of the C-Ca-Cb-Cg dihedral of the Histidine 52 side chain, along the simulation production, for both Gal-1 with Histidine 52 in mono-protonated (red greyscales) and di-protonated (blue greyscales) states.

For a better insight into the biochemical basis of the differential susceptibility of human white cells to Gal-1-induced death, binding of biotinylated Gal-1 was analyzed at the different pH conditions under study (FIG. 5B). Gal-1 binding was significantly lower at pH 6 than at physiological pH (pH 7.4), normally employed for in vivo assays. As a way to understand the interactions responsible for the change in Gal-1 affinity for lactose observed at low pH, a set of fluorescence spectroscopy experiments with different pH and ligand concentrations was performed (FIG. 5C). Results conclusively showed that Gal-1 binding to the disaccharide lactose decreases with pH. The curves additionally demonstrated that the lectin activity decreased dramatically at a pH falling below 6.

To understand the biochemical mechanisms behind the evident loss of Gal-1 activity in acidosis, the present study was undertaken to analyze the structural determinants of Gal-1, focusing on the protonation state of certain amino acids by NMR spectroscopy.

A detailed view of the Gal-1 ligand binding groove (the protein region where ligand recognition and binding takes place) is shown in FIG. 5D, and the presence of two histidine residues interacting with the carbohydrate moiety should be taken into special consideration. It has been shown that histidine side chains often take part into ligand recognition, providing a plausible regulatory mechanism under physiological conditions due to their intrinsic pKa (FIG. 5E).

For a solvent-exposed histidine, the expected pKa value is approximately 6.3, but it may change depending on the secondary, tertiary and quaternary protein structure. NMR spectroscopy was used to evaluate both the tautomeric and the protonation states of each particular histidine at pH values between 5 and 8, and the corresponding pKa of His44 and His52 in the Gal-1 sequence. These studies showed that the environment of both histidines is different, reflected by their spectra (FIG. 5G). For Histidine 52, the obtained values remained close to the canonical pKa and tautomer ratio, thus indicating it is a residue fully exposed to the solvent. However, the pKa for the complex Gal-1-Lac decreased to 5.9, suggesting that the residue was involved in interactions with the lactose ring, which is obstructed its exposure to the solvent. On the other hand, Histidine 44, located in the S4 strand, was involved in a hydrogen-bond contact with the ligand. In the Gal-1 free state, this histidine showed a pKa of 5.7, with a slight decrease in the population of the epsilon tautomer, indicating that the residue establishes weak interactions with the tertiary structure environment, as reported. The pKa value and tautomer composition of Histidine 44 overcame a sudden change upon lactose binding. The pKa of bound Gal-1:Lactose for Histidine 44 was 4.2, evidencing its implication in critical interactions with the ligand moiety that protects the residue from direct contact with the solvent environment.

To better understand the relationship between structural modifications produced by a change in the pH and the binding affinity regulation mechanisms, molecular dynamics simulation of the pH-dependent structural changes in the Gal-1 structure and their relation to ligand binding of the carbohydrate recognition domain were performed. These simulations resulted stable, as shown by the root mean square deviation (RMSD) versus time plot using the starting X-ray PDBid=1GZW structure as a reference (not shown).

A main difference for mono-protonated and di-protonated Histidine 52 was evidenced within the loop between S4 and S5 strands by molecular dynamics simulations (FIG. 5F). Namely, the presence of a di-protonated side chain for Histidine 52 affects the loop dynamics, inducing a wider movement. This was shown by the amplitude explored by the projection of the first essential mode with major contribution in motion, as derived from MD simulations for the protein in both states. This looser conformation was found to interfere directly with the correct positioning of the lactose ring in the ligand binding groove. Furthermore, upon di-protonation, the dihedral angle describing the Histidine 52 side chain orientation was prompt to explore a different configuration (FIG. 5H). Visual inspection of that newly explored conformation in simulation running showed that this orientation interferes with the correct lactose ring stacking. Therefore, the results demonstrate that at low pH, the loop containing the di-protonated state of Histidine 52 presents more flexibility and the residue side chain rotates and moves towards the solvent, acquiring an "open" conformation. The swinging out of Histidine 52 side chain impedes correct ligand positioning in the binding groove, whereas in the Histidine 52 mono-protonated state, its configuration in the loop ensures correct ligand stacking.

Results of this study revealed an interesting interplay between the environmental pH, the conformation of the loop containing Histidine 52, and the ligand binding affinity. Also confirmed was the involvement of Histidine 52 and its protonation equilibrium in the decline of Gal-1 ligand binding affinity.

D. Example 3

Generation of Gal-1 Polypeptide Variants Resistant to Deactivation by Oxidation and Acidosis Based on the results of the acidosis investigation conducted in Example 2, six mutants were generated using site-directed mutagenesis, and further tested for their pro-apoptotic activity and susceptibility to acidosis conditions. The mutants were the following:

H52Y, H52N, H52Q, H52R, H44Y, and H44N.

These six mutants were successfully produced, but variants mutated in H44X and not H52R could not be properly purified as they did not display binding to the affinity column (lactosyl-sepharose). Additionally, the H52Q mutant was not employed in further evaluation assays due to its recently discovered lower binding activity for lactose than that of WT Gal-1. See Hiramatsu et al., "INVOLVEMENT OF HISTIDINE RESIDUES IN THE pH-DEPENDENT β-GALACTOSIDE BINDING ACTIVITY OF HUMAN GAL-1," *Biochemistry* (2013). The same publication also confirmed the low lactose binding affinity of the H44Q mutant.

Of the remaining mutants, H52Y and H52N demonstrated affinity for β-galactosides comparable to WT Gal-1. In order to test these Gal-1 variants and their affinity to complex N-glycans, a solid phase assay with immobilized asialofetuin was performed. The assay results showed that both H52Y and H52N mutants maintained their binding affinity at lower pH (FIGS. 6A-6D), and these results were further confirmed by measurement of the dissociation constant ($K_{id}$) values for both mutants at pH=7.5, 6.5, and 5.5, using intrinsic fluorescence intensity (FIG. 6E).

Figure 6:
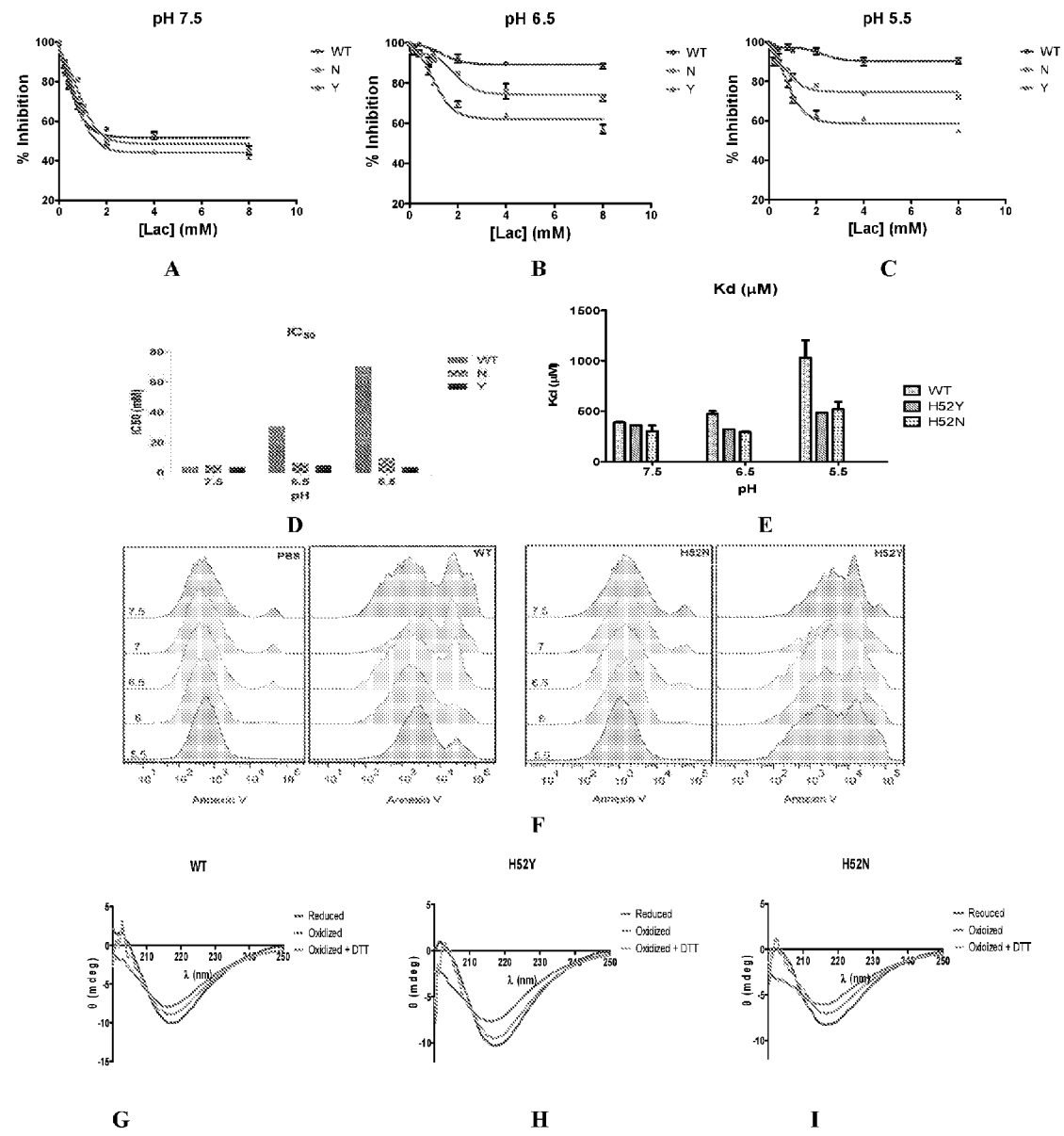
FIGS. 6A-6D show characterization of acid resistant Gal-1 polypeptide variants based on solid phase competition assays with immobilized asialofetuin/lactose for WT Gal-1 and acidic pH-resistant Gal-1 variants, H52N (N) and H52Y (Y), at pH 7.5 (FIG. 6A), pH 6.5 (FIG. 6B), and pH 5.5 (FIG. 6C). IC50 values (50% inhibitory concentration) for each mutant variant at different pH, based on in vivo testing of SG2 in an EAE model, are shown in FIG. 6D.
FIG. 6E shows Gal-1:lactose dissociation constant ($K_d$) values determined by fluorescence spectroscopy at pH=7.5, 6.5, and 5.5, respectively.
FIG. 6F shows the pro-apoptotic effect of Gal-1 on T cell lines as a function of pH.
FIGS. 6G-I show Far-UV CD spectra of the freshly prepared reduced form (Reduced), air oxidized form (Oxidized), and oxidized form treated with DTT (Oxidized+DTT) WT Gal-1 (FIG. 6G), H52N mutants (FIG. 6H), and H52Y mutants (FIG. 6I).

Cell death assays were also performed for testing the pro-apoptotic effect of the mutants under different pH conditions (FIG. 6F). Although Gal-1 was found to induce apoptosis of human activated T-cells in all cases, this effect substantially decreased under acidic pH conditions for the WT Gal-1 and the Gal-1 variant H52N, but not for Gal-1 variant H52Y, thus supporting that the pro-apoptotic activity of this mutant is not affected by an acidic environment within the range tested.

However, as expected, the His mutants (H52Y and H52N) were found not to be resistant to oxidation (FIGS. 6G-I). Therefore, additional testing was conducted in an attempt to identify a mutant also having the desired resistance to oxidative inactivation. The apoptotic activity of reduced or oxidized WT Gal-1, as well as the 6 different Cys to Ser mutants generated in Example 1 (C2S, C16S, C42S, C60S, C88S, C130S), is illustrated in FIG. 3. As shown, only those mutants lacking Cys2, Cys16, and Cys88 were able to elicit T-cell apoptosis in oxidizing conditions, reaching similar apoptosis values as the reduced WT Gal-1.

Thus, the following two Gal-1 double mutant variants were further generated: C2S-C16S and C2S-C88S. These mutants were resistant to oxidative inactivation, in addition to the six previously prepared $C_xS$ single mutants. In fact, the C2S-C16S and C2S-C88S mutants showed almost no changes on their circular dichroism spectra after oxidation (FIG. 2), suggesting no conformational changes under conditions that deactivate WT Gal-1, due to lacking two of the critical cysteines involved in deactivation.

Additional analysis was conducted as to the impact of oxidation on the structure and function of Gal-1 using T-cell death assays. Specifically, as shown in FIG. 3, activated T-cells were exposed to different Gal-1 concentrations under reducing or oxidative conditions. Oxidation of the WT Gal-1 resulted in loss of the pro-apoptotic activity, while the Gal-1 double mutants (C2SC16S and C2SC88S) did not change the apoptotic effect on T-cells, irrespective of the prevalent redox condition.

From all of the Gal-1 variants tested by biophysical assays, it was demonstrated that H52N and H52Y were resistant to pH. Table 3 below sets forth the best Gal-1 variants (acid resistant (AR) or oxidation resistant (OR)) that were designed and expressed.

TABLE 3

| rhGal-1 variant | Acid-resistance | Oxidation resistance |
| --- | --- | --- |
| H52Y (AR) | + | − |
| H52N (AR) | + | − |
| C2S C16S (OR) | − | + |
| C2S C88S (OR) | − | + |

E. Example 4

Generation of SuperGal Variants Resistant to Deactivation by Oxidation and Acidosis with Enhanced Immunomodulating Properties To still overcome the pH dependency and oxidative inactivation of Gal-1 based on the results of Examples 1-3, the following triple mutants were additionally generated from the combination of the two mutants resistant to acidic pH (H52Y and H52N) and the two mutants resistant to oxidation (C2SC88S and C2SC116S): C2SC16SH52Y, C2SC16SH52N, C2SC88SH52Y, and C2SC88SH52N. These new mutants were called SuperGal-1 ("SG1"), Super-Gal-2 ("SG2"), SuperGal-3 ("SG3"), and SuperGal-4 ("SG4"), respectively.

Figure 7:
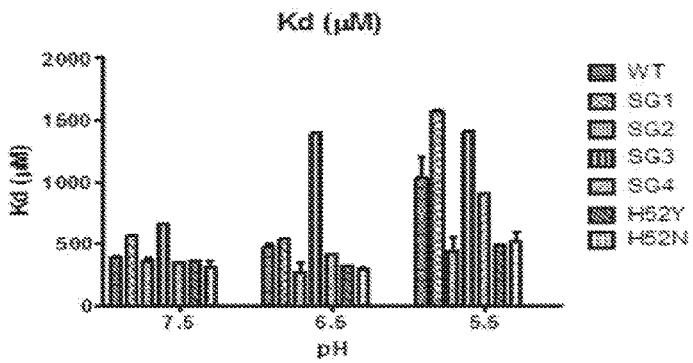
FIG. 7 shows Gal-1:lactose dissociation constant ($K_d$) values as determined by fluorescence spectroscopy at pH=7.5, 6.5, and 5.5.

These mutants were expressed and purified using lactosyl sepharose, resulting in yields as follows:

SGal-1 (SG1): C2S C16S H52N—yield: 42 mg
SGal-2 (SG2): C2S C16S H52Y—yield: 43 mg SGal-3 (SG3): C2S C88S H52N—yield: 37 mg
SGal-4 (SG4): C2S C88S H52Y—yield: 110 mg The mutants were evaluated using the same in vitro methodologies used for the previously described mutants. Starting by in vitro assays with intrinsic fluorescence intensity as a function of lactose concentration, the Gal-1:lactose dissociation constant (Kd) values were determined at pH=7.5, 6.5, and 5.5. As can be seen in FIG. 7, SG1 and SG3 had poor performance at pH 6.5 and 5.5, whereas SG2 and SG4 retained their affinity for lactose independently of pH. To evaluate the additional resistance to oxidation as compared to WT Gal-1, the four triple mutants SGXs were exposed to air (5 days), and the Far-UV CD spectra were recorded. The mutants SG1, SG2, SG4, and SG4 demonstrated resistance to the adverse effects of acidic pH and oxidation condition, as summarized in Table 4 below.

TABLE 4

| Name | Mutations | Resistance to acidic pH | Resistance to oxidative conditions |
| --- | --- | --- | --- |
|  | H52Y | + | − |
|  | H52N | + | − |
|  | C2S C16S | − | + |
|  | C2S C88S | − | + |
| SG1 | H52N C2S C16S | + | + |
| SG2 | H52Y C2S C16S | + | + |
| SG3 | H52N C2S C88S | + | + |
| SG4 | H52Y C2S C88S | + | + |

Figure 8:
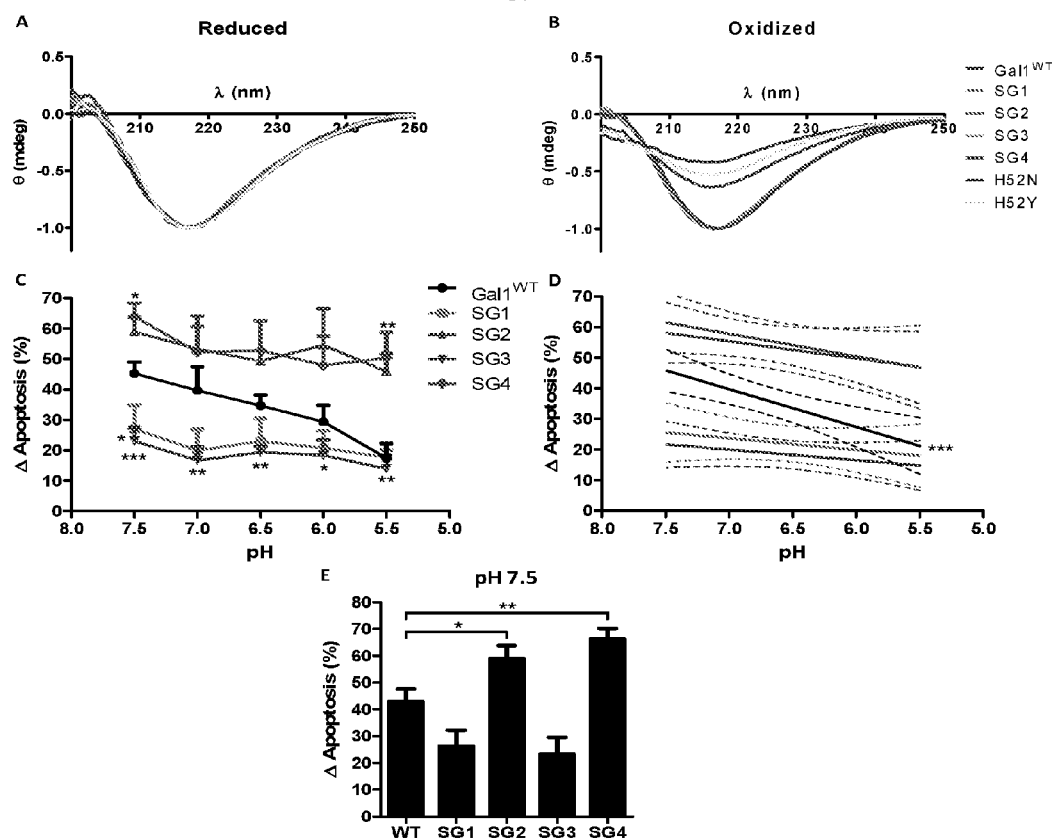
FIGS. 8A and 8B show Far-UV CD spectra of reduced and air oxidized mutant variants of WT Gal-1: the four triple mutant variants triple mutants (SG1, SG2, SG3, SG4) and the two single mutants (H52Y and H52N). Specifically.
FIG. 8C shows percentage of apoptosis of Jurkat cells after 6 hours of incubation in RPMI medium with a buffer at pH 7.5, 7.0, 6.5, 6.0, or 5.5, in the presence of vehicle (saline) or 5 µM of WT Gal-1 or the SG1, SG2, SG3, or SG4 mutants. The quantified percentage of apoptosis is based on staining with Annexin-V-FITC and evaluated by flow cytometry. The results are representative of 6-10 independent experiments. Stars indicate significant differences with the WT variant, except for those located below SG1 and SG3 values, which indicate differences between those variants and SG2 and SG4 variants.
FIG. 8D is a linear regression model of the result of FIG. 8C.
FIG. 8E shows quantified percentage values of susceptibility to apoptosis of Jurkat cells incubated for 6 hours in RPMI medium at pH 7.5 in the presence of vehicle (saline) or 5 µM of WT Gal-1 or the variants SG1, SG2, SG3, or SG4.
FIG. 8F shows apoptotic capacity of Gal-1 variants at pH 7.5 based on pooled data from at least three experiments that assessed (by Annexin-V-FITC staining) and analyzed (by flow cytometry) apoptosis of mouse T cells that were incubated for 6 hours with 5 µM WT Gal-1, H52Y, H52N, SG1, SG2, SG3, or SG4 mutant variants. $\Delta$ % Apoptosis=[% Apoptosis with Treatment−% Apoptosis with PBS].
FIG. 8G shows apoptosis induction by Gal-1 variants in acidic conditions compared to physiological pH based on apoptosis (assessed by Annexin-V-FITC staining and analyzed by flow cytometry) of T cells incubated for 6 hours with 5 µM of WT Gal-1, H52Y, H52N, SG1, SG2, SG3, or SG4 mutant variants in RPMI media at pH 7.5 or 5.5. Percentage of loss of activity was determined by 100*[($\Delta$ % Apoptosis at pH 7.5−$\Delta$ % Apoptosis at pH 6)/$\Delta$ % Apoptosis at pH 7.5].
FIG. 8H shows IL-10 secretion of splenocytes induced by Gal-1 variants, the splenocytes being isolated from C57BL/6 mice and incubated in complete RPMI with PBS and 5 µM of WT Gal-1 or "SuperGal-1" variants 1, 2, 3, or 4 (SG1, SG2, SG3, or SG4), with the supernatants being collected after 48 hours and the secreted IL-10 measured by ELISA.
FIG. 8I shows IL-27 secretion of dendritic cells induced by SuperGal variants, the dendritic cells being differentiated from C57BL/6 mice bone marrow precursors with recombinant GM-CSF during 9 days, and incubated in complete RPMI with PBS and 3 µM of WT Gal-1, SG1, SG2, SG3, or SG4, with the supernatants being collected after 24 hours and the secreted IL-27 measured by ELISA.
Figure 8:
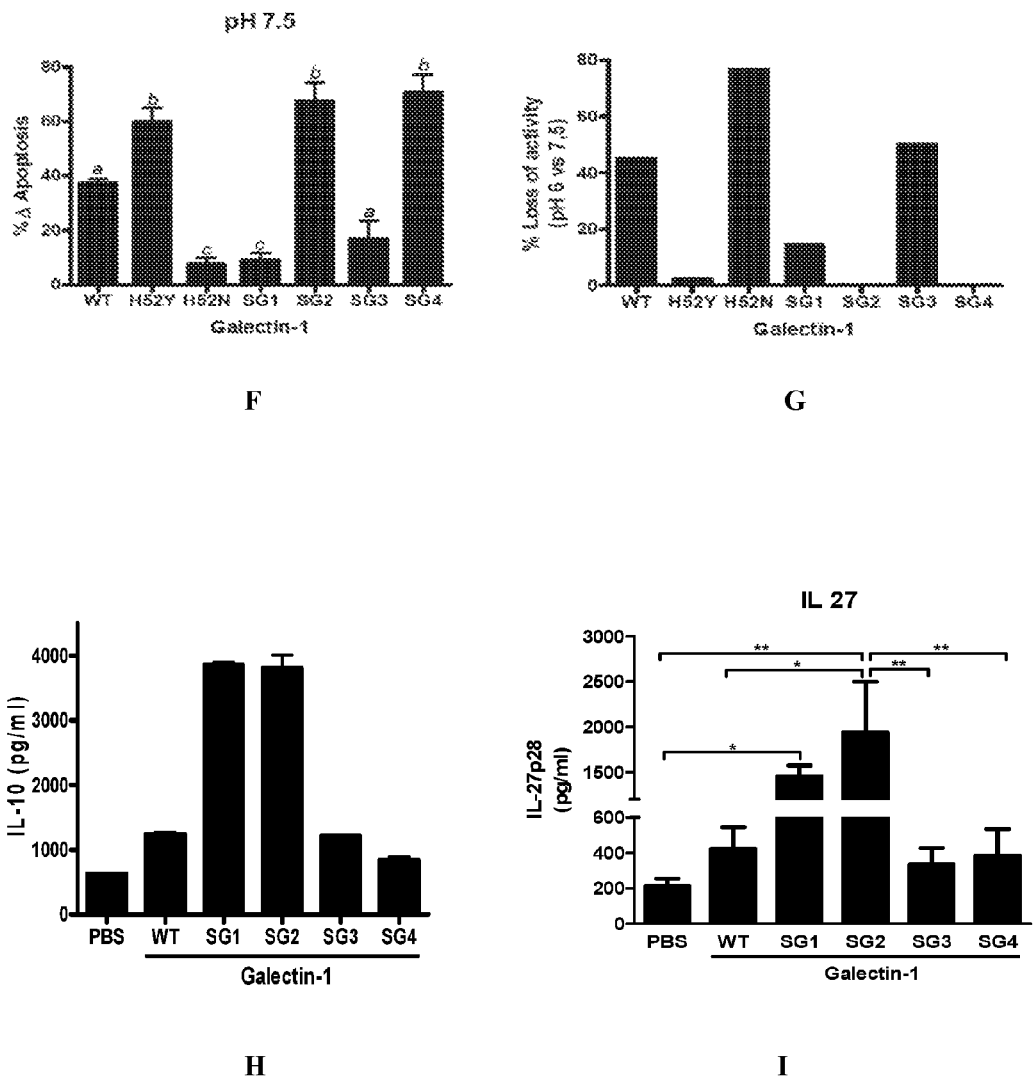

Once produced and purified using lactosyl-Sepharose affinity column, several studies were conducted. First, based on eh effects of oxidation in the secondary structure, previously observed on the acid-resistant variants H52N and H52Y, the effects of oxidative conditions on the new mutants were evaluated. By circular dichroism it was observed that, while WT-Gall, H52N and H52Y were susceptible to oxidation (10 mM $H_2O_2$), adding the C2SC16S or C2SC88S mutations to these variants provides them with new resistance properties, as evidenced by a similar spectrum in reducing and oxidizing conditions shown in FIGS. 8A and 8B. Specifically, under physiological conditions (reducing environment), all of the new variants showed the same circular dichroism spectrum, which implies that the combination of any three modifications does not alter the secondary structure of Gal-1 (FIG. 8A). Notably, as shown in FIG. 8A, all four SGXs (or SuperGals) showed almost identical CD spectra for reduced and oxidized conditions.

After verifying resistance to oxidative conditions of the SuperGal variants, additional studies were conducted to verify whether resistance to acidic conditions was also preserved in these variants. Induction of apoptosis of activated T cells was evaluated at different pH levels in the presence of 5 μM WT Gal-1 and the variants SG1, SG2, SG3, or SG4. Similarly to the previously described H52N and H52Y mutants, the pro-apoptotic activity of the WT Gal-1 variant was observed to gradually decrease as the pH became more acidic, whereas the SuperGal variants were capable of inducing a similar percentage of apoptosis over all tested pH levels (FIGS. 8C and 8D). In addition, different SuperGal variants recapitulated at acidic pH similar to the activity previously observed for the H52Y variant. In contrast, the variants SG1 and SG2—displaying the H52N mutation—showed low pro-apoptotic capacity at physiological pH, similar to that observed for the H52N variant (FIGS. 8C and 8D). As further shown in FIGS. 8F and 8G, H52Y and the SuperGal variants 2 and 4 (SG2 and SG4, which contain the mutation H52Y) exhibit a significantly enhanced ability to induce apoptosis of T cells when compared to WT Gal-1 at physiological conditions (pH 7.5). Additionally, single mutant H52Y and SuperGal variants 2 and 4 were found to maintain unaltered capacity to induce apoptosis of T cells in acidic conditions (pH 6) compared to physiological conditions (pH 7.5). In contrast, WT Gal-1, H52N, SG1 and SG3 (which contain the mutation H52N) showed a considerable reduction of this biological function.

In addition to high resistance to acidic pH, it was found that combining the H52Y variant with those variants providing resistance to oxidation unexpectedly results double resistant mutants demonstrating synergistic effects at physiological conditions. Specifically, as shown in FIG. 8E, the SG2 and SG4 variants demonstrate pro-apoptotic activity in a significantly higher amount than that of the WT Gal-1 at pH 7.5.

Evaluation of Immunomodulating Properties of SuperGal Variants

The synergistic effects observed for SG2 and SG4 variants under physiological conditions with respect to WT Gal-1 prompted further investigation into whether any other immune regulatory effect, in addition to T cell apoptosis, may account for the superior biological effects of these new variants. Thus, based on the previously shown modulation of this tolerogenic cytokine by WT Gal-1 in both murine and human cells (Toscano et al., GALECTIN-1 SUPPRESSES AUTOIMMUNE RETINAL DISEASE BY PROMOTING CONCOMITANT TH2 AND T REGULATORY-MEDIATED ANTI-INFLAMMATORY RESPONSES, *Immunol.*, 176(10): 6323-32 (2006); Van der Leij et al., DIMERIC GALECTIN-1 INDUCES IL-10 PRODUCTION IN T-LYMPHOCYTES: AN IMPORTANT TOOL IN THE REGULATION OF THE IMMUNE RESPONSE, *Pathol.*, 204(5): 511-18 (2004); Stowell et al., DIFFERENTIAL ROLES OF GALECTIN-1 AND GALECTIN-3 IN REGULATING LEUKOCYTE VIABILITY AND CYTOKINE SECRETION, *J. Immunol.*, 180(5): 3091-102 (2008); Cedeno-Laurent et al., GALECTIN-1 TRIGGERS AN IMMUNOREGULATORY SIGNATURE IN TH CELLS FUNCTIONALLY DEFINED BY IL-10 EXPRESSION, *J. Immunol.*, 188(7): 3127-37 (2012); and Perone et al., SUPPRESSION OF AUTOIMMUNE DIABETES BY SOLUBLE GALECTIN-1, *J. Immunol.*, 182(5): 2641-53 (2009)), the ability of Gal-1 to induce secretion of IL-10 was evaluated.

In a first set of tests, each of the SuperGal variants was tested for the capacity to induce secretion of anti-inflammatory cytokines and turn on regulatory mechanisms. As previously reported, Gal-1 treatment can induce secretion of IL-10 in both CD4 and CD8 T cells, and IL-27 in dendritic cells (Ilarregui et al., *Nat. Immunol.*, 10:981-991 (2009)). Accordingly, in this study, splenocytes were isolated from C57BL/6 mice, and T cells were activated with soluble anti-CD3e and anti-CD28, and then treated with 5 uM WT Gal-1 or the SuperGal variants. After 48 hours, secretion levels to the culture media of IL-10 were measured (FIG. 8H). Likewise, dendritic cells were differentiated from bone marrow precursors with recombinant GM-CSF and treated with 3 uM WT Gal-1 or the SuperGal variants. After 24 hours, secretion levels to the culture media of IL-27 were measured (FIG. 8I). Secretion of both anti-inflammatory cytokines, IL-10 and IL-27, was significantly enhanced by SG1 and SG2 when compared to WT Gal-1. On the other hand, variants SG3 and SG4 induced secretion of IL-10 and IL-27 in levels comparable to WT Gal-1. Finally, SG1 and SG2 induced a 4-fold increase of IL-10 secretion compared to WT Gal-1 induction, and a 10-fold increase of IL-27 secretion compared to WT Gal-1 induction.

In still additional studies, splenocytes were obtained from 8-12 week old C57BL/6 mice. In order to activate the T cells, the samples were incubated for 8 hours at physiological pH conditions in the presence of 3 µM WT Gal-1 or G1, SG2, SG3 and SG4 variants, and anti-CD3E and anti-CD28 soluble agonist antibodies. After 2 days, supernatant was harvested and levels if IL-10 were measured by both in-plate conventional ELISA and flow cytometry CBA (Cytokine Bead Array) techniques.

TABLE 5

|  | Control | WT | SG1 | SG2 | SG3 | SG4 |
|---|---|---|---|---|---|---|
| Mean | 155 | 521 | 2500 | 2512 | 246 | 289 |
| SD | 10 | 187 | 504 | 645 | 171 | 70 |
| p (vs WT) | * | — | *** | *** | ns | ns |

Figure 9:
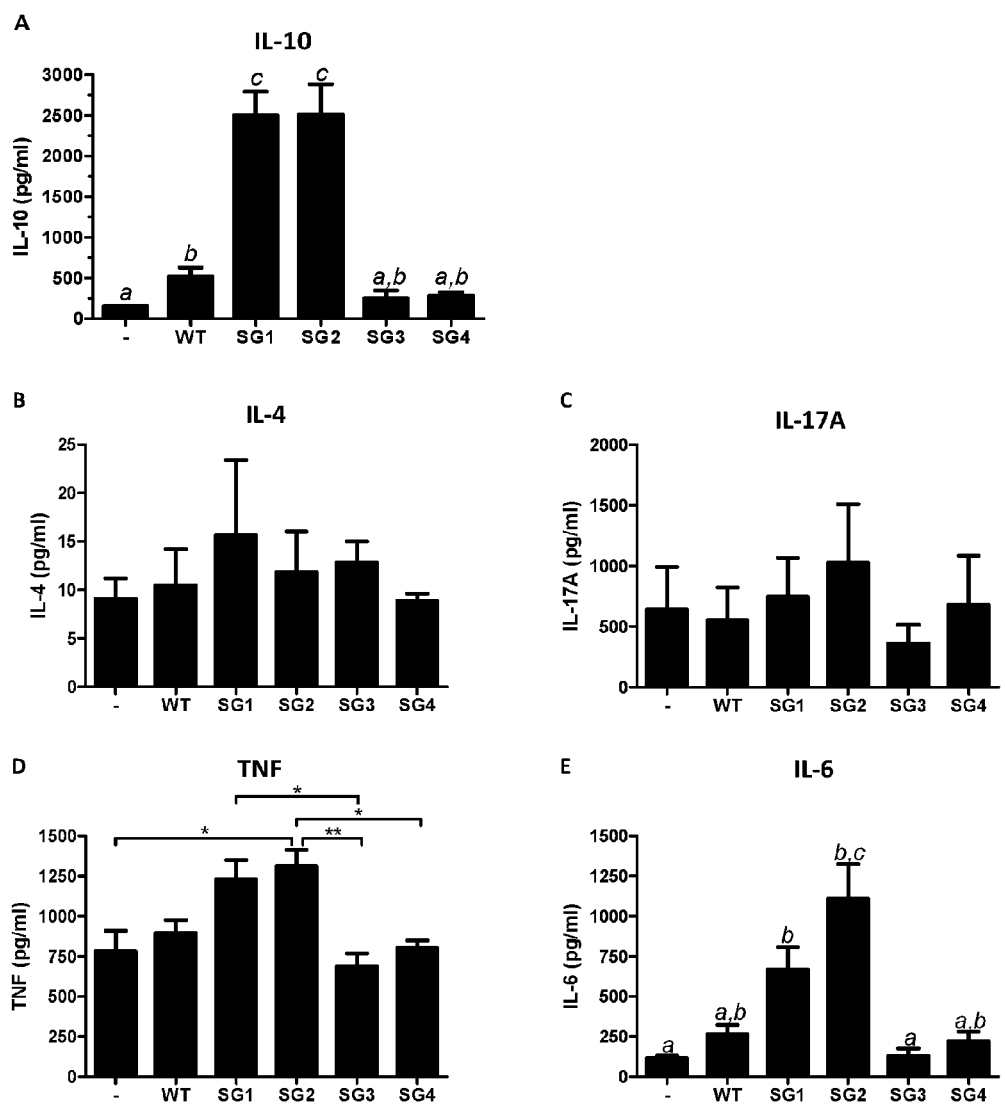
FIG. 9A-E show levels of secretion of IL-10, IL-4, IL17A, TNF, and IL-6 respectively, in supernatants from spleen cells stimulated for 48 hours with anti-CD3E agonist antibodies and anti-soluble CD28 (1 µg/ml) in the presence of 3 µM of WT Gal-1 or the variants SG1, SG2, SG3, or SG4. The results represent 3 independent experiments.

As shown in Table 5 above and FIG. 9A, WT Gal-1 induced a 3.36 time increase in the secretion of IL-10 (521±10 pg/ml, WT vs. PBS) in agreement with prior studies (Stowell et al., (2008)), whereas the SG1 and SG2 variants induced a secretion of IL-10 that was 16.2 times higher than the control and 4.8 times higher than WT variant (2500±504 and 2512±645 pg/ml, respectively). This was however not observed in the SG3 and SG4 variants. Further analysis of the secretion levels of other cytokines by flow cytometry CBA showed no differences in the levels if IL-4 and IL-17A.

Although no differences were found in TNF levels between WT Gal-1 and the SuperGal variants, SG2 induced a significant increase in TNF compared to the control (FIGS. 9B-9D). Additionally, although WT Gal-1 doubled the amount of IL-6 secreted by cells when compared to the control, FIG. 9E shows that the presence of SG2 induced a significant increase of this cytokine, an effect not observed with the other variants. Aside from this particular cytokine, the major difference in cytokine secretion induced by variants SG2 and SG1 was observed for IL-10, the secretion levels of which increased 2 and 4 times more than that for IL-6 (2512 and 2500 vs. 1109 and 669 pg/ml, respectively).

Table 6 below provides secretion levels of the different cytokines tested in relation to the induced levels by treatment with the WT variant. Of all the cytokines tested, secretion of IL-10 was more dramatically up-regulated when compared to secretion obtained with WT Gal-1.

TABLE 6

| Cytokine | SG1 | SG2 | SG3 | SG4 |
|---|---|---|---|---|
| IL-10 | 4.80 | 4.82 | 0.47 | 0.55 |
| IL-4 | 1.5 | 1.13 | 1.23 | 0.85 |
| IL-17A | 1.36 | 1.89 | 0.65 | 1.23 |
| TNF | 1.37 | 1.46 | 0.77 | 0.9 |
| IL-6 | 2.54 | 4.21 | 0.49 | 0.83 |

Notably, SuperGal variants containing the H52Y mutations (SG2 and SG4) were found to induce higher apoptosis, regardless of the cysteine mutations. In terms of IL-10 secretion by T lymphocytes, the C16S mutation (SG1 and SG2) contributed to the higher effect, regardless of the mutation at position 52.

Ability of SuperGal Variants to Induce Tolerogenic Dendritic Cells

Galectin-1 has been shown to generate IL-27-producing tolerogenic dendritic cells which contributed to expansion of IL-10-producing Tr1 lymphocytes (Ilarregui et al., *Nat. Immunol.* (2009); Poncini et al., TRYPANOSOMA CRUZI INFECTION IMPARTS A REGULATORY PROGRAM IN DENDRITIC CELLS AND T CELLS VIA GALECTIN-1-DEPENDENT MECHANISMS, *Immunol.,* 195(7): 3311-24 (2015)). Based on these findings, studies were conducted to evaluate whether the Gal-1 variants resistant to acidic pH and oxidation also induced tolerogenic dendritic cells.

Bone marrow precursors were obtained from 8-12 week old C57BL/6 mice, and differentiated for 9 days in the presence of recombinant GM-CSF, as described. Unlike the protocol used by Ilarregui et al, in which WT Gal-1 was present from the beginning of the differentiation process, the objective of the study was to determine whether the new variants could induce secretion of IL-27 in already differentiated, immature dendritic cells. Thus, in 9-days fully-differentiated dendritic cells, following phenotyping these cells (CD11c+CD86$^{low}$MHC-II$^{low}$), immature dendritic cells were incubated in the presence of 304 WT Gal-1 or the SGs variants. After 24 hours, the supernatant was harvested and IL-27p28 and determined by ELISA.

Figure 10:
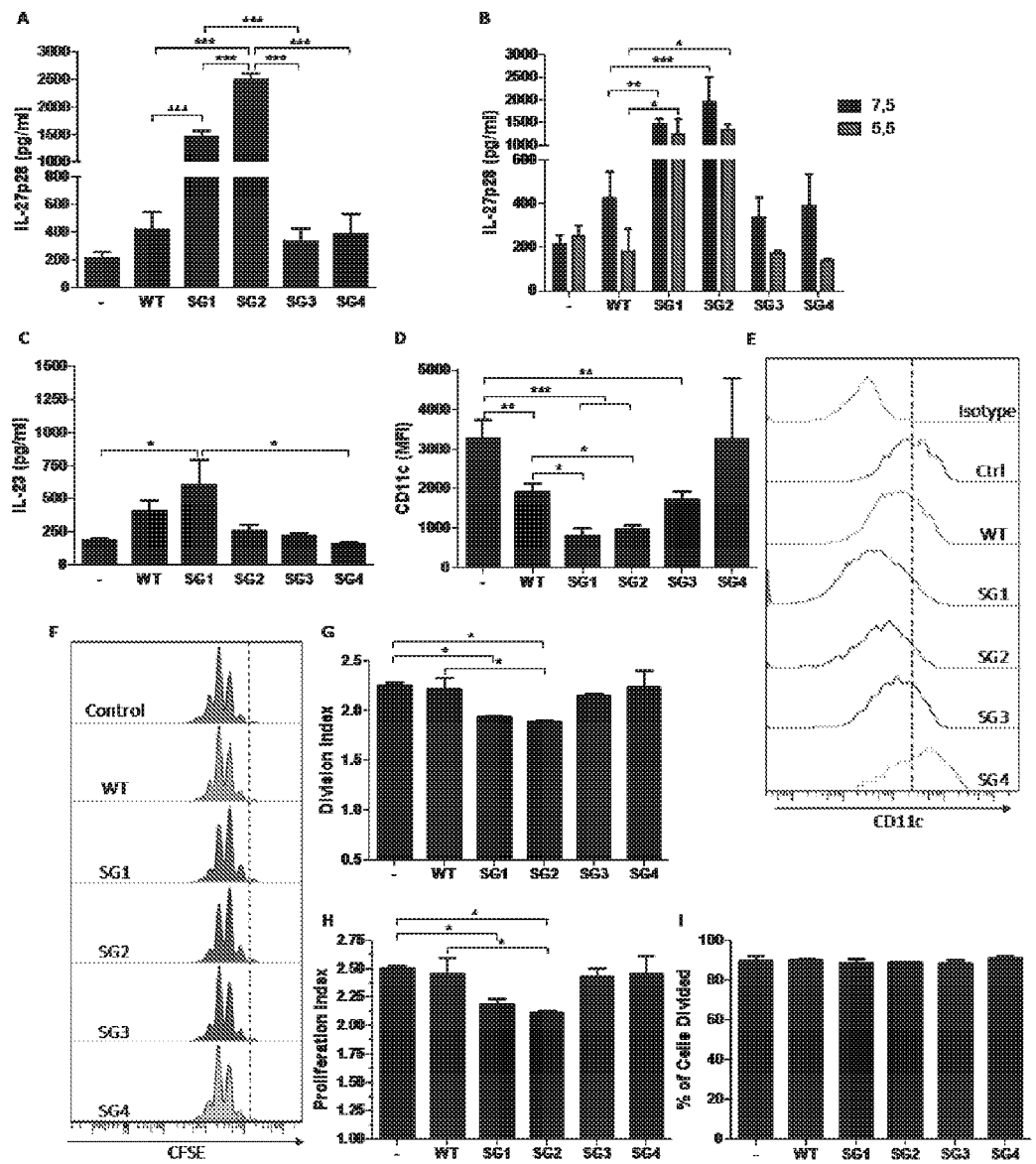
FIGS. 10A-10C show levels of IL-27p28 and IL23 in supernatants of dendritic cells incubated for 24 hours in complete medium alone or with 3 µM of WT Gal-1 or the variants SG1, SG2, SG3, or SG4, with buffer adjusted at pH 7.5 or 5.5.
FIGS. 10D and 10E show determination and the expression of CD11c by flow cytometry on dendritic cells cultured for 72 hours in complete medium alone or in the presence of 3 µM of WT Gal-1 or the variants SG1, SG2, SG3, or SG4.
FIG. 10F shows the proliferation assessed by dilution of the fluorescent dye CFSE by flow cytometry of spleen CD4+ T lymphocytes purified from the spleen and co-cultured with LPS-induced dendritic cells for 72 hours together with agonistic anti-CD3E before exposure to dendritic cells pre-incubated for 72 hours in complete medium alone (control) or supplemented with 3 µM of WT Gal-1 or the variants SG1, SG2, SG3, or SG4.
FIG. 10G shows the division index.
FIG. 10H shows the proliferation.
FIG. 10I shows the percentage of dividing cells, based on the results of FIG. 10F.

Similar to the effect observed for IL-10, it was found that whereas treatment with the WT variant doubled basal levels of IL-27 by dendritic cells (421±124 vs 211±44 pg/ml), both SG1 and SG2 variants induced a more pronounced increase in the levels of secretion of this cytokine, significantly higher than those generated by the WT (1453±120 and 2494±165 pg/ml, respectively) (FIG. 10A). Furthermore, secretion levels induced by SG2 were still significantly higher than those generated by SG1. This effect was only demonstrated for variants containing the C16S mutation, since it was not observed for SG3 and SG4 variants (FIG. 10A).

The fact that the SuperGal variants induced T cell apoptosis regardless of pH variations prompted further evaluation of whether the ability of these new variants to induce IL-27 secretion was also preserved even in acidic microenvironments. For this purpose, the above experiments were repeated, but the dendritic cells were incubated at pH 7.5 or 5.5. While WT Gal-1 lost its ability to induce IL-27 secretion from dendritic cells at acidic pH, treatment with the SG1 or SG2 variants led to similar levels of IL-27 secretion at both physiological or acidic pH, being significantly higher than those induced by WT Gal-1 at each respective pH (FIG. 10B).

Ability of SuperGal Variants to Induce Secretion of Pro-Inflammatory Cytokines

The ability of the SuperGal variants to induce secretion of pro-inflammatory cytokines, such as IL-23 (which, in contrast to IL-27, favors Th17 responses), was also evaluated. Dendritic cells were again incubated under similar conditions. As shown in FIG. 10C, the SuperGal variants did not increase IL-23 secretion as compared with WT Gal-1, which itself induced a small increase compared to control. However, the SG1 variant induced a slight increase of IL-23 compared to WT Gal-1, showing a significant difference with the control. However, levels of secreted IL-23, even after SG1 treatment, were well below the levels of induction of IL-27 for SG1 (603±191 vs 1453±120 pg/ml, respectively).

In addition to IL-27 and IL-10 secretion, an important hallmark of tolerogenic dendritic cells is the low expression of CD11c on the cell surface (Ilarregui et al., *Nat. Immunol.* (2009)). To evaluate changes in this cell surface marker, dendritic cells were differentiated from bone marrow precursors and, following a 72-hour incubation period in the absence or presence of 3 μM of WT Gal-1 or SG1, SG2, SG3 or SG4 variants, levels of CD11c expression were analyzed by flow cytometry. While the dendritic cells significantly decreased levels of CD11c upon incubation with WT Gal-1, the cells treated with SG1 and SG2 variants showed even lower expression of this marker on their cell surface (FIGS. 10D and 10E). Moreover, although the SG3 variant induced a decrease in CD11c expression similar to that generated by the WT variant, the SG4 mutant showed non-consistent results.

In order to confirm the tolerogenic nature of dendritic cells treated with WT Gal-1 or the SG variants, purified CD4+ T cells from spleens of C57BL/6 mice, loaded intracellularly with CFSE fluorescent molecule, were co-cultured with dendritic cells that had been previously pulsed with LPS (immunogenic stimulus) and agonistic anti-CD3E soluble for a 72-hour period, in the presence of dendritic cells that had been previously treated for a 72-hr period with PBS or 3 μM of WT Gal-1, or SG1, SG2, SG3 or SG4. After 4 days in culture, proliferation was analyzed by flow cytometry based on the CFSE fluorescence dilution. As shown in FIGS. 10F and 10G, only dendritic cells that had been previously treated with SG1 and SG2 variants were able to decrease proliferation of CD4+ lymphocytes induced by LPS-treated dendritic cells—an effect evidenced by a significantly lower division index. As further shown in FIGS. 10H and 10I, these differences were not due to the ability of dendritic cells treated with SG1 or SG2 to overcome T cell activation (as evidenced by a similar percentage of dividing cells in all cases), but affected the process of further proliferation based on the significantly lower observed proliferation rate. Furthermore, only dendritic cells treated with the SG2 mutant, which also secrete higher levels of IL-27, showed significantly higher differences compared to dendritic cells treated with WT Gal-1.

The results, summarized in Table 7 below, support the conclusion that the new SuperGal variants are not only resistant to oxidative and acidic pH conditions, but also have enhanced immunoregulatory activity. The mutations introduced into these variants successfully uncoupled two different immunoregulatory activities (i.e., induction of T cell apoptosis versus secretion of immunosuppressive cytokines, and induction of tolerogenic dendritic cells). While the SG2 and SG4 variants displayed enhanced pro-apoptotic activity, the SG1 and SG2 variants induced higher secretion of both IL-10 in T lymphocytes and IL-27 in dendritic cells.

TABLE 7

| ACTIVITY | WT GAL-1 | SG1 | SG2 | SG3 | SG4 |
|---|---|---|---|---|---|
| Apoptosis | + | − | +++ | − | +++ |
| IL-10/IL-27 | + | +++ | +++ | −/+ | −/+ |

Evaluation of Augmented Immunoregulatory Activity of SuperGal Variants In Vivo

Figure 11:
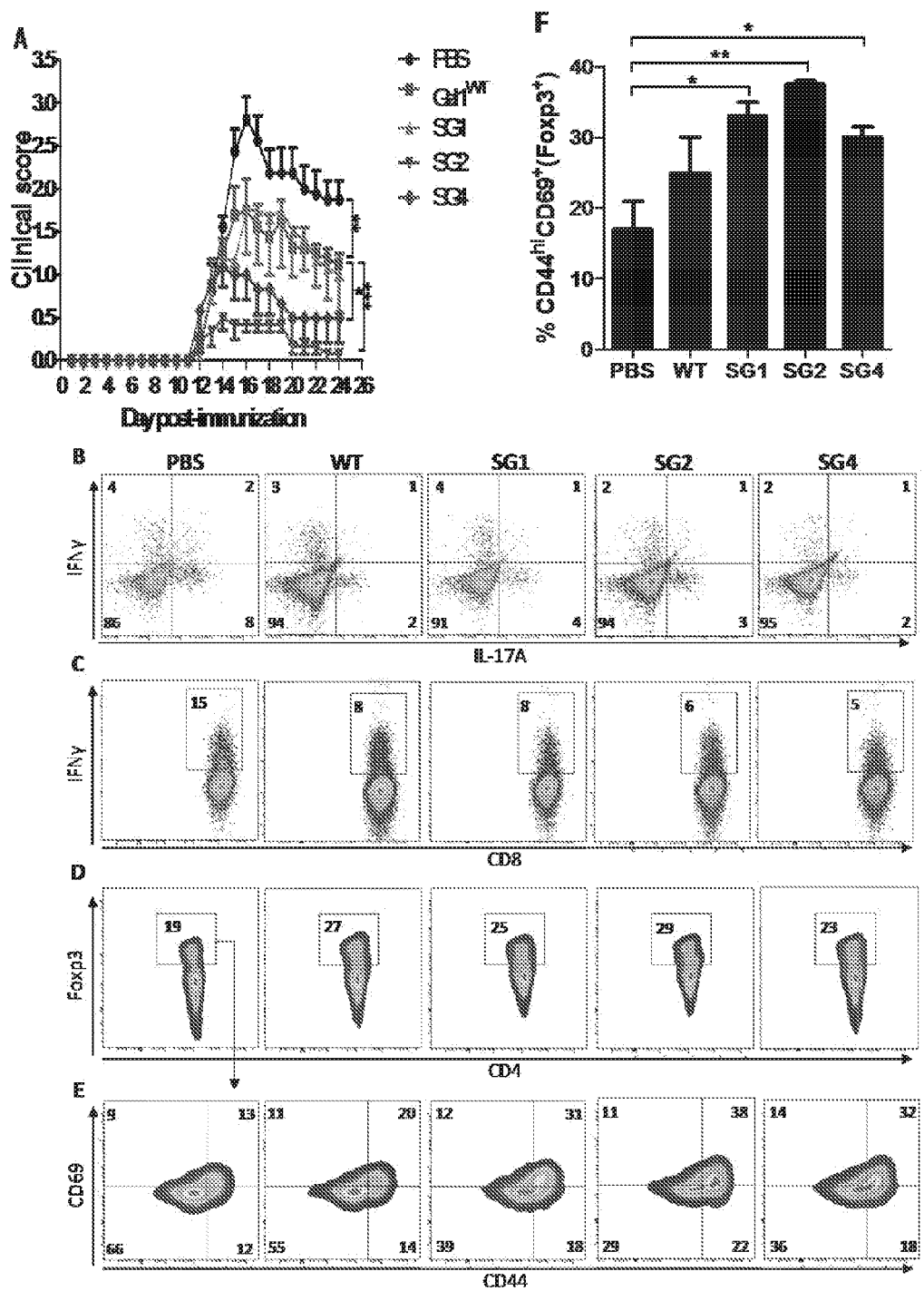
FIG. 11A shows clinical scores of EAE mice treated with vehicle (PBS) or 100 µg per mouse/day of WT Gal-1 or the variants SG1, SG2, SG3, or SG4 from the date of first symptoms. The results are of 2 independent experimental groups, with 5 mice per group per experiment.
FIGS. 11B and 11C show expression levels of IL-17A and/or IFN-γ by flow cytometry of CD4+ or CD8+ cells from draining lymph node from immunization site, re-stimulated in vitro for 48 hours with 30 µg/ml of MOG35-55 and agonist anti-CD3E (1 µg/ml).
FIG. 11D shows Foxp3 expression levels by flow cytometry of CD4+ cells from draining lymph node from immunization site at day 24 post-immunization.
FIG. 11E shows expression levels of CD69 and CD44 by flow cytometry of CD4+Foxp3$^+$ cells as evaluated by flow cytometry.
FIG. 11F shows quantification of the results obtained in FIG. 11E.

EAE was induced in 8-12 weeks old C57BL/6 WT mice by immunizing with myelin-oligodendrocyte glycoprotein 55 (MOG55) (as described in Toscano et al., *Nat. Immunol.* (2007)), and WT Gal-1 or SG variants were administered following a therapeutic protocol. When animals showed the first signs of disease (weakness in the tail) they were randomly treated by injection with 100 μg/day of WT Gal-1 or SG1, SG2 or SG4 variant. The SG3 variant was not tested because it did not show evidence in vitro of an enhanced immunoregulatory capacity with respect to WT Gal-1. The clinical scores of mice were assessed daily until day 24 post-immunization. Animals were then sacrificed for ex vivo assays. While treatment with the SG1 variant generated a similar effect on disease course as treatment with WT Gal-1, mice treated with the SG4 or SG2 variants showed significantly less severe clinical signs than the group treated with WT Gal-1. As shown in FIG. 11A, the effects of treatment with the SG2 variant were even more pronounced than those observed after SG4 treatment. Interestingly, mice treated with the SG2 variant, the mutant that showed the best performance in vitro, developed a very mild and attenuated disease.

Twenty four days after immunization, cells from draining lymph were purified and re-stimulated in vitro for 48 hours in the presence of MOG35-55. As shown in FIGS. 11B and 11C, treatment with WT Gal-1 or SG1, SG2 and SG4 variants decreased the percentage of Th1, Th17 cells and IFN-γ-producing CD8+ T cells in vivo compared to control mice. Both of the variants SG4 and SG2, which showed the best performance with regards to amelioration of clinical signs of the disease, were also the most successful in reducing these three pathogenic populations. Although SG1 was able to reduce the percentage of IFN-γ+-producing CD8+ T cells and IL-17A-producing CD4+ T cells, its effects with respect to Th1 were not as pronounced. This effect could be explained by the ability of these SuperGal variants to induce high secretion of IL-27, which is an anti-Th17 but pro-Th1 cytokine.

Effects of SuperGal Variants on T Regulatory Cells

As observed from the results in FIG. 11D, all Gal-1 variants induced an increase in the percentage of CD4+ Foxp3$^+$ T Regulatory Cells (Tregs). However, a detailed analysis of the activation state of these cells further showed that, while WT variant induced an increased percentage of Foxp3+ cells with an activation profile characterized by expression of CD69 and high levels of CD44 (CD44hiCD69+), the SG1 and SG4 variants, as well as the SG2 variant, unexpectedly induced an even greater increase in the percentage of Treg CD44hiCD69+ when compared to WT Gal-1, leading to a significantly higher frequency of Tregs generated in the absence of treatment.

Based on an analysis of clinical signs of the disease (the clinical score) and the immune correlates, SG2 appears as the best possible candidate to achieve therapeutic responses. Based on these findings, the therapeutic potential of this specific SuperGal variant was further evaluated in a short protocol pre-clinical treatment.

Figure 13:
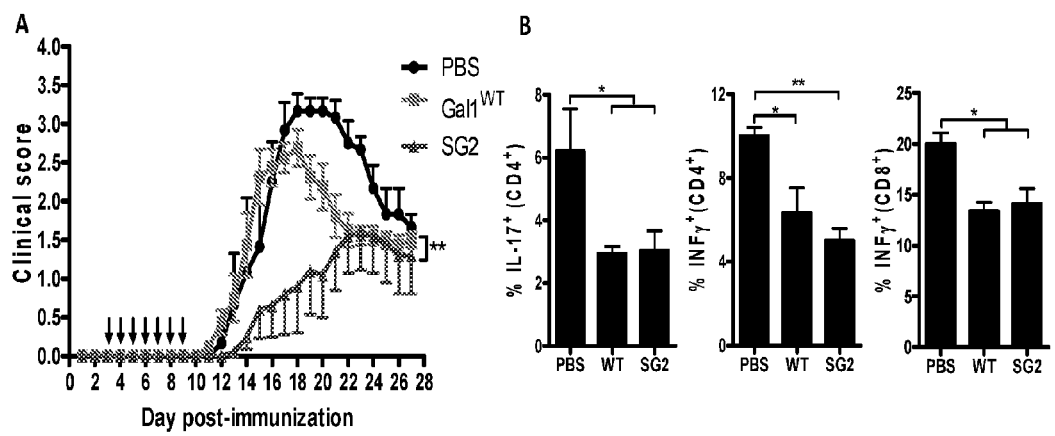
FIG. 13A shows the clinical score of EAE mice treated with vehicle PBS (control) or 100 µg per mouse/day of WT Gal-1 (red-greyscales) or the SG2 variant (blue-greyscales) from days 3 to 9 post-immunization.
FIG. 13B shows quantification of CD4$^+$ T cells producing IL-17A or IFN-γ, and CD8+ T cells producing IFN-γ in draining lymph nodes obtained 27 days post-immunization and re-stimulated in vitro with 30 µg/1 of MOG35-55, as evaluated by flow cytometry.

EAE was induced in WT mice that were further treated with 100 μg/day WT Gal-1 or the SG2 variant for 1 week starting at days 3-9 post-immunization. As shown in FIG. 13A, treatment with the SG2 variant for a period limited to one week prior to first symptoms of the disease led to a significantly less severe disease than treatment with WT Gal-1. Even more, evolution of the disease was substantially different, showing absence of acute stage but reaching a similar chronic stage than observed for other groups. At day 27 post-immunization, when all groups were in the chronic stage of the disease, mice were sacrificed and T cell responses were analyzed after in vitro re-stimulation of purified cells from draining lymph nodes. Treatment with both Gal-1 variants induced a significant reduction in the percentage of IFN-γ-producing CD8+ T cells as well as Th17 and Th1 cells, effects that were even more apparent following treatment with the SG2 variant (FIG. 13B).

Altogether, these data additionally demonstrate that SuperGal-1 variants SG1, SG2 and SG4 present enhanced immunoregulatory capacity as evidenced by their apoptosis of pathological T cells (SG2 and SG4), secretion of IL-10 on T cells (SG1 and SG2) and secretion of IL-27 on dendritic cells (SG1 and SG2).

Figure 12:
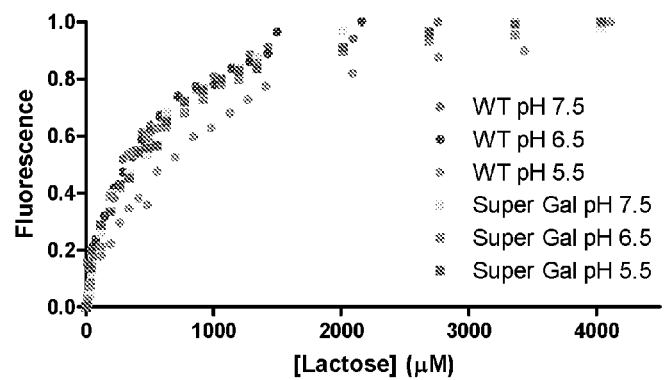
FIG. 12 shows lactose binding to Gal-1 at different pH conditions as a function of lactose concentration, tested by fluorescence. Trp68 in the ligand binding groove was used as probe, $\Delta$exc=295 nm, and $\lambda$em=345 nm.

Considering all the results described above, the variants SG1, SG2 and SG4 of the invention are the best performing Gal-1 variants in vitro. SG2 and SG4 showed an affinity for (3-galactoside residues comparable to WT Gal-1 at physiological pH (7.5), and maintained its affinity for lactose at acidic pH (6.5 and 5.5), while WT Gal-1 was not able to do so. This was additionally tested by fluorescence intensity (FIG. 12). An immunomodulatory activity of SG2 was also evaluated in experimental autoimmune encephalomyelitis, an animal model for multiple sclerosis. As shown in FIG. 13A treatment with the novel SG2 mutant resulted in lower clinical scores compared to WT Gal-1 and control-treated mice (FIG. 13A), additionally confirming that resistance to pH and oxidation results in improved biological activity.

Of note, SG1 exhibits an enhanced capacity to induce secretion of anti-inflammatory cytokines (IL-10 and IL-27), thus promoting a tolerogenic environment without inducing T cell death; whereas SG4 activates T cell death programs without augmenting anti-inflammatory cytokines (IL-10 and IL-27). On the other hand, SG2 triggers both immunoregulatory pathways. These different profiles of the SGXs (referred to as "SuperGal" mutants or variants herein) may be exploited therapeutically to offer different therapeutic advantages by activating either one or both of these mechanisms depending on the nature of each autoimmune disease.

The above results evidence that the "SuperGal" variants of Gal-1 exhibit higher resistance to oxidative conditions when compared to WT Gal-1, and that lactose binding in an oxidative environment presents no significant difference for any of the triple mutants. Furthermore, taking all of the results (Examples 1-4) together, the results confirm that mutations of H52, C2, C16 and/or C88 in the Gal-1 polypeptide provide resistance to acidic pH and oxidative conditions. SuperGals (SGs), which not only showed resistance to both oxidation and acidic pH, but also showed a significantly enhanced immunoregulatory activity (T cell apoptosis and secretion of tolerogenic/immunosuppressive cytokines). Finally, in vivo results demonstrate the applicability of these SuperGal variants, and particularly SG2, as therapeutic agents for treatment and prophylaxis of autoimmune diseases.

D. Other Embodiments

The detailed description set forth above is provided to aid those skilled in the art in practicing the invention. However, the invention described and claimed herein is to be limited in scope by the specific embodiments described above, as these embodiments are presented as mere illustrations of several aspects of the invention. Any combinations and modifications of the described methods and components, and compositions used in the practice of the methods, in addition to those not specifically described, will become apparent to those skilled in the art based on the present disclosure and do not depart from the spirit or scope of the present invention. Such variations, modifications, and combinations are also encompassed by the present disclosure and fall within the scope of the appended claims.

What is claimed is:

1. A Gal-1 polypeptide variant, comprising:
a mutation of the histidine residue corresponding to position 52 of the full-length amino acid sequence of native human Gal-1 as shown in SEQ ID NO: 1, the mutation being a substitution of the histidine to tyrosine or asparagine,
wherein the Gal-1 polypeptide variant is resistant to acidic conditions of an inflammatory microenvironment that otherwise result in deactivation of native human Gal-1.

2. A nucleic acid encoding a Gal-1 polypeptide variant having a mutation of the histidine residue corresponding to position 52 of the full-length amino acid sequence of native human Gal-1 as shown in SEQ ID NO: 1, the mutation being a substitution of the histidine to tyrosine or asparagine,
wherein the Gal-1 polypeptide variant is resistant to acidic conditions of an inflammatory microenvironment that otherwise result in deactivation of native human Gal-1.

3. A pharmaceutical composition, comprising:
the Gal-1 polypeptide variant of claim 1, or a fragment thereof; and
a pharmaceutically acceptable carrier.

4. The Gal-1 polypeptide variant of claim 1, further comprising a mutation of the cysteine residue corresponding to a position selected from 2, 16, 88, or combinations thereof of the full-length amino acid sequence of native human Gal-1, the further mutation being a substitution of the cysteine to serine,
wherein the Gal-1 polypeptide variant is resistant to acidic and oxidative conditions of an inflammatory microenvironment that otherwise result in deactivation of native human Gal-1.

5. The Gal-1 polypeptide variant of claim 4, wherein the mutation the cysteine residue corresponds to positions 2 and 16 or 2 and 88 of the full-length amino acid sequence of native human Gal-1.

6. The Gal-1 polypeptide variant of claim 4, wherein the mutation of the cysteine reside corresponds to positions 2 and 16 of the full-length amino acid sequence of native human Gal-1.

7. The Gal-1 polypeptide variant of claim 6, wherein the variant exhibits a synergistic effect at physiological pH with respect to resistance to acidic and oxidative conditions and pro-apoptotic activity compared to a Gal-1 polypeptide variant without the mutation of the cysteine residue.

8. The polypeptide variant of claim 6, wherein the polypeptide variant induces secretion of IL-10 at least 16 times higher than secretion of IL-10 induced by native human Galectin-1.

9. A pharmaceutical composition, comprising:
the Gal-1 polypeptide variant of claim 4, or a fragment thereof; and
a pharmaceutically acceptable carrier.

10. A method for modulating an immune response, comprising:
contacting an immune cell with the Gal-1 polypeptide variant of claim 1, wherein the Gal-1 polypeptide variant modulates the immune response by up-regulating binding of the Gal-1 polypeptide or a fragment thereof to its natural binding partner(s) under acidic conditions of an inflammatory microenvironment that otherwise inhibit the binding of native human Gal-1 or a fragment thereof to its natural binding partner(s).

11. The method of claim 10, wherein the contacting occurs in vivo.

12. The method of claim 10, wherein the immune cell is a mammalian cell.

13. The method of claim 1, wherein the acidic conditions result in an extracellular pH falling below 7.0 and the oxidative conditions inhibit lactose binding of the cysteine residues of native human Gal-1.

14. The method of claim 1, wherein the immune response is down-regulated.

15. A method for treating a subject having a condition in need of down-regulation of an immune response, comprising:
administering to the subject a therapeutically effective amount of a Gal-1 polypeptide variant that binds to natural binding partner(s) of native human Gal-1 under inflammatory conditions,
wherein the Gal-1 polypeptide variant is administered in a therapeutically effective amount for down-regulation of the immune response to treat the condition in need of down-regulation of the immune response, and comprises:
a first mutation of the histidine residue corresponding to position 52 of the full-length amino acid sequence of native human Gal-1 as shown in SEQ II) NO: 1, the mutation constituting a substitution of the histidine to tyrosine or asparagine; and
at least one second mutation of the cysteine residue corresponding to a position selected from 2, 16, 88, or combinations thereof of the full-length amino acid sequence of native human Gal-1 as shown in SEQ ID NO:1, the at least one second mutation constituting a substitution of the cysteine to serine.

16. The method for treating a subject according to claim 15, wherein the subject is a human and the condition is an immune disorder selected from the group consisting of acute or chronic inflammatory disease, auto-immune disease, allergic disorder, arthritis, hepatitis, asthma, multiple sclerosis, transplant rejection, graft-versus-host disease (GVHD), inflammatory bowel disease, Parkinson's disease, Alzheimer's disease, and any organ-specific autoimmune disease.

17. The method for treating a subject according to claim 15, comprising administering the Gal-1 polypeptide variant as an active compound of a pharmaceutical composition that comprises a pharmaceutically acceptable carrier.

18. The method for treating a subject according to claim 17, wherein the pharmaceutical composition is administered to the subject in a dosage form selected from the group consisting of tablets, capsules, pills, powders, granules, parenteral solutions or suspensions, oral solutions or suspensions, oil-water emulsions, intravenous injections, and gene therapy.

19. The method for treating a subject according to claim 15, wherein the Gal-1 polypeptide variant down-regulates the immune response of the subject by inducing secretion of anti-inflammatory cytokines IL-10 and IL-27.

20. The method for treating a subject according to claim 15, wherein the Gal-1 polypeptide variant down-regulates the immune responses of the subject by inducing apoptosis of T cells without augmenting secretion of anti-inflammatory cytokines IL-10 and IL-27.

* * * * *